(12) United States Patent
Masubuchi et al.

(10) Patent No.: US 10,653,433 B2
(45) Date of Patent: May 19, 2020

(54) MEDICAL DEVICE AND METHOD FOR TREATMENT

(71) Applicant: TERUMO KABUSHIKI KAISHA, Shibuya-ku, Tokyo (JP)

(72) Inventors: Yuuki Masubuchi, Kanagawa (JP); Masaomi Imai, Kanagawa (JP); Takashi Kitaoka, Kanagawa (JP); Takahiro Chida, Kanagawa (JP); Kazuaki Kanamoto, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 448 days.

(21) Appl. No.: 15/439,005

(22) Filed: Feb. 22, 2017

(65) Prior Publication Data

US 2017/0238948 A1    Aug. 24, 2017

(30) Foreign Application Priority Data

Feb. 23, 2016    (JP) .................................. 2016-031782

(51) Int. Cl.
*A61B 17/22* (2006.01)
*A61B 17/3207* (2006.01)

(52) U.S. Cl.
CPC ...... *A61B 17/22* (2013.01); *A61B 17/320725* (2013.01); *A61B 17/320758* (2013.01);
(Continued)

(58) Field of Classification Search
CPC ................................ A61B 2017/22051; A61B 2017/22065–22067; A61B 17/320758–320775; A61B 2017/22038–2017/22098; A61B 17/22; A61B 17/3207–2017/320791; A61M 25/0021–0029; A61M 25/0032; A61M 2025/0034; A61M 2025/0037; A61M 2025/0183; A61M 2025/0188; A61M 2025/0177; A61M 2025/1056;
(Continued)

(56) References Cited

U.S. PATENT DOCUMENTS 6,142,987 A    11/2000   Tsugita
6,165,199 A *  12/2000   Barbut .................. A61B 17/22
                                                          604/22

(Continued)

*Primary Examiner* — Katrina M Stransky
*Assistant Examiner* — Brigid K Byrd
(74) *Attorney, Agent, or Firm* — Buchanan Ingersoll & Rooney PC

(57) ABSTRACT

Provided is a medical device designed to be inserted into a lumen of a living body, the medical device including: a long shaft part; and a cylindrical hollow body. The shaft part has a center axis at position which differs from a center axis of the hollow body on a cross section perpendicular to the center axis of the shaft part. The hollow body has a housing part extending along the center axis of the hollow body, the hollow body being a groove depressed from an outer peripheral surface to an inner peripheral surface or a slit penetrating from an outer peripheral surface to an inner peripheral surface. The shaft part is positioned between inner surfaces facing from the outer peripheral surface to the inner peripheral surface in such a way that at least a portion of the shaft part constitutes the slit or the groove of the housing part.

20 Claims, 20 Drawing Sheets

(52) U.S. Cl.
CPC ............... *A61B 17/320783* (2013.01); *A61B 2017/22038* (2013.01); *A61B 2017/22039* (2013.01); *A61B 2017/22065* (2013.01); *A61B 2017/22067* (2013.01); *A61B 2017/22079* (2013.01); *A61B 2017/320716* (2013.01); *A61B 2017/320775* (2013.01)

(58) Field of Classification Search
CPC .......... A61M 29/00; A61F 2/01; A61F 2/013; A61F 2002/011; A61F 2220/00; A61F 2/95–97

See application file for complete search history.

(56) References Cited

U.S. PATENT DOCUMENTS

| | | | | |
|---|---|---|---|---|
| 2002/0049423 | A1* | 4/2002 | Howell | A61B 18/14 604/528 |
| 2004/0254528 | A1* | 12/2004 | Adams | A61M 25/00 604/96.01 |
| 2005/0209610 | A1* | 9/2005 | Carrison | A61B 17/1671 606/114 |
| 2007/0233174 | A1* | 10/2007 | Hocking | A61F 2/013 606/200 |
| 2016/0066932 | A1* | 3/2016 | Root | A61B 17/12036 606/194 |

* cited by examiner

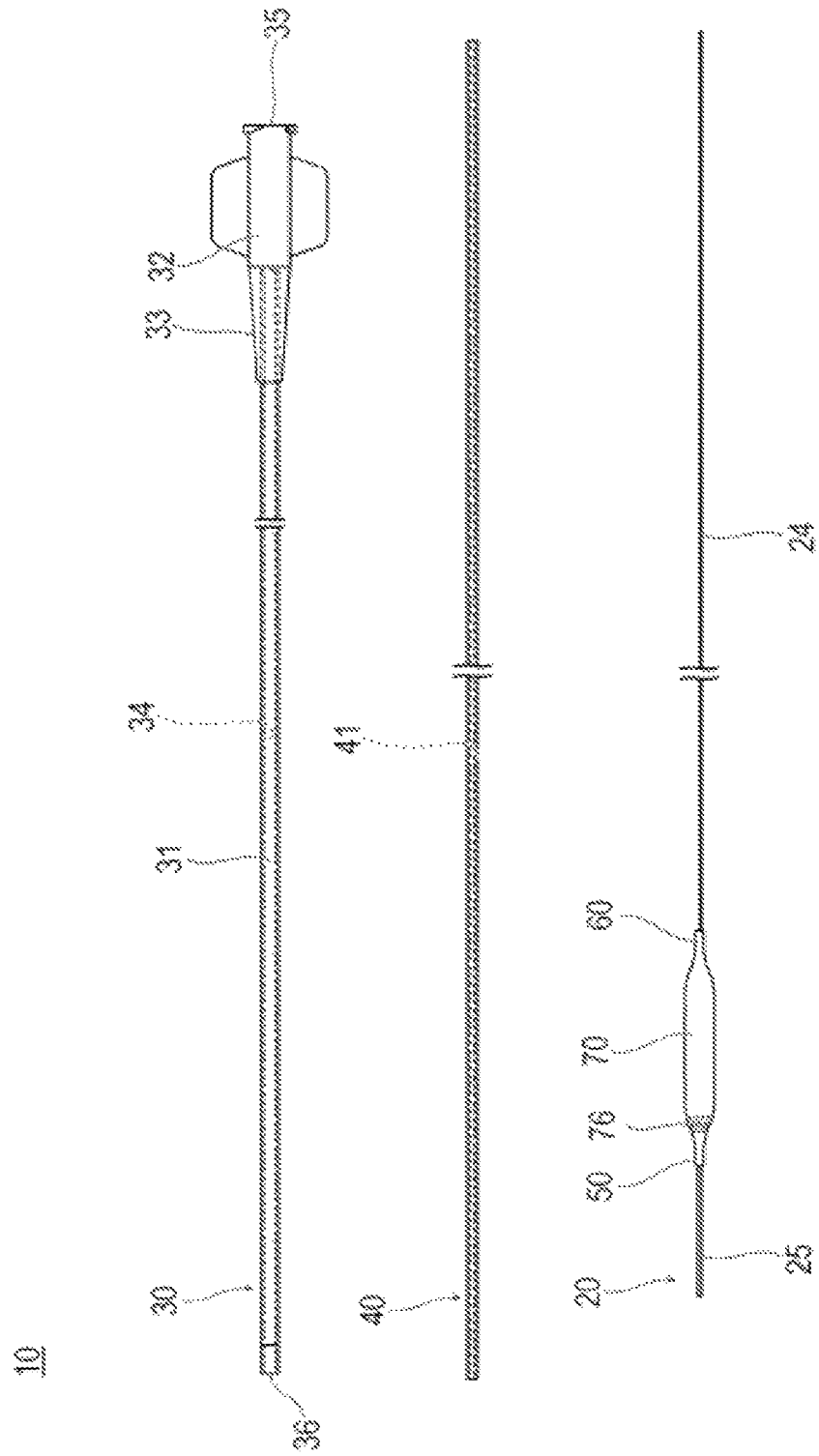

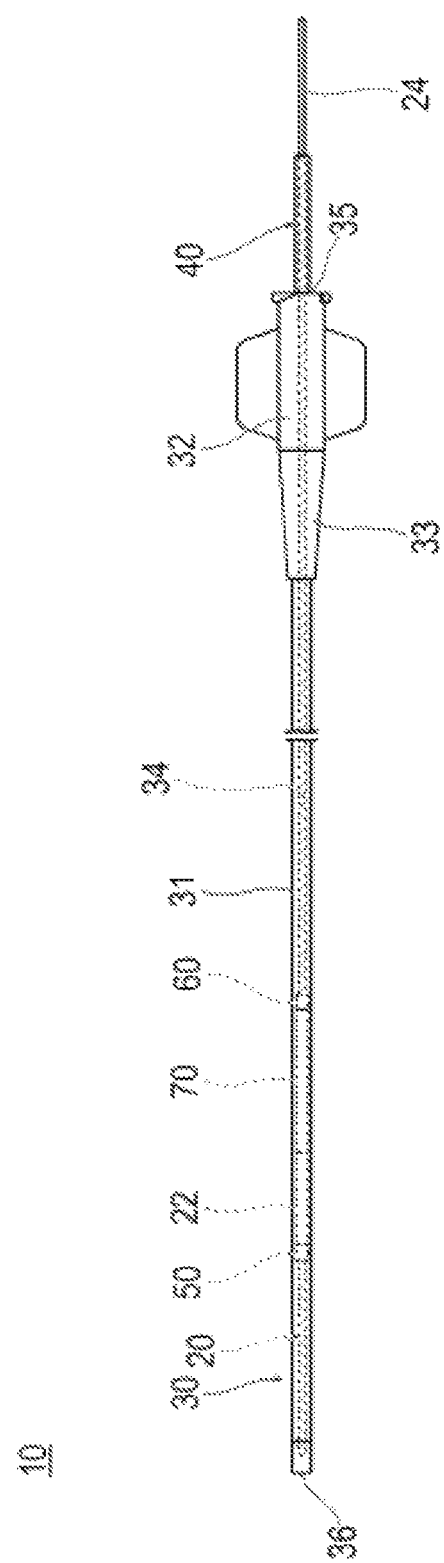

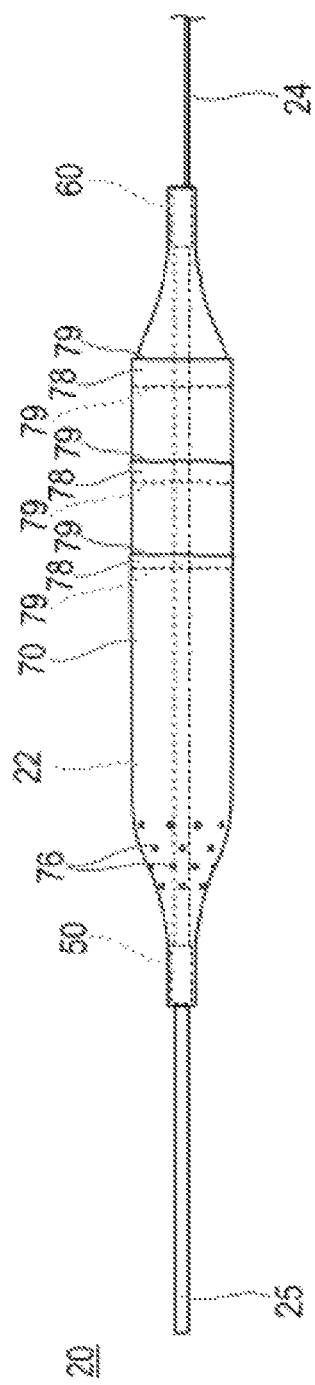
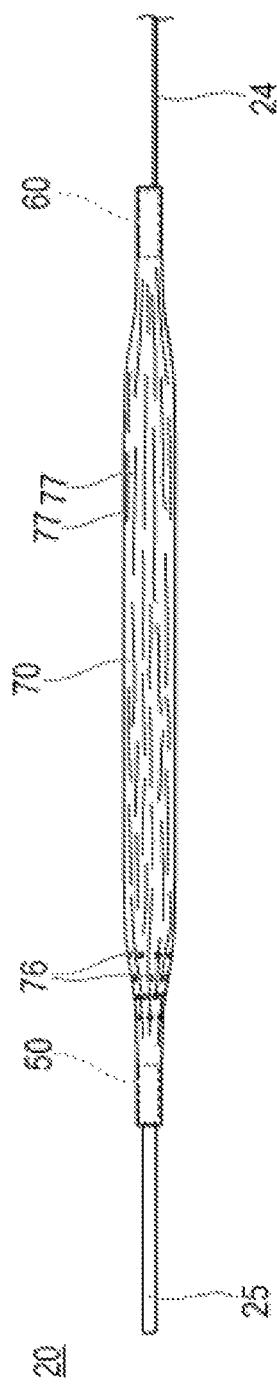
FIG. 3A
FIG. 3B

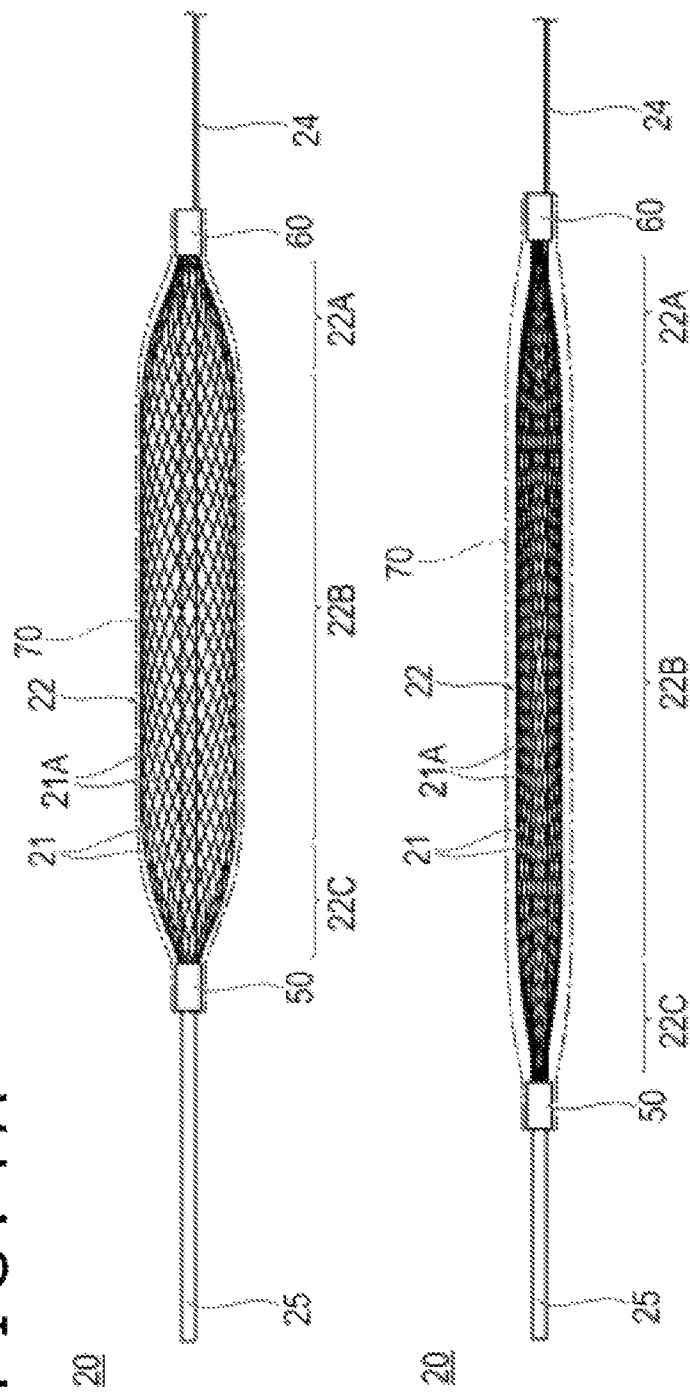

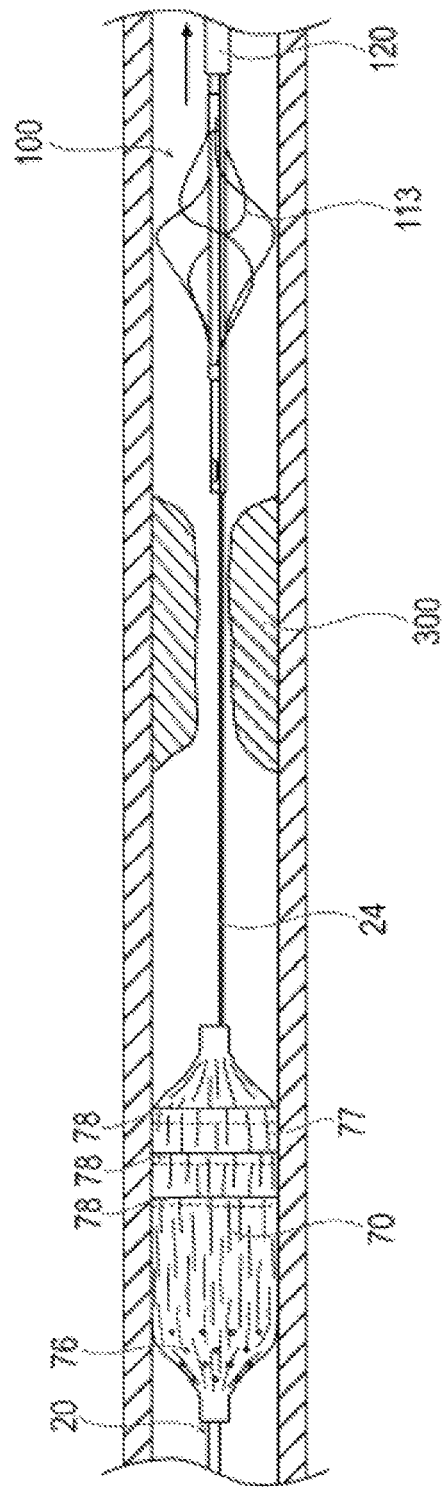

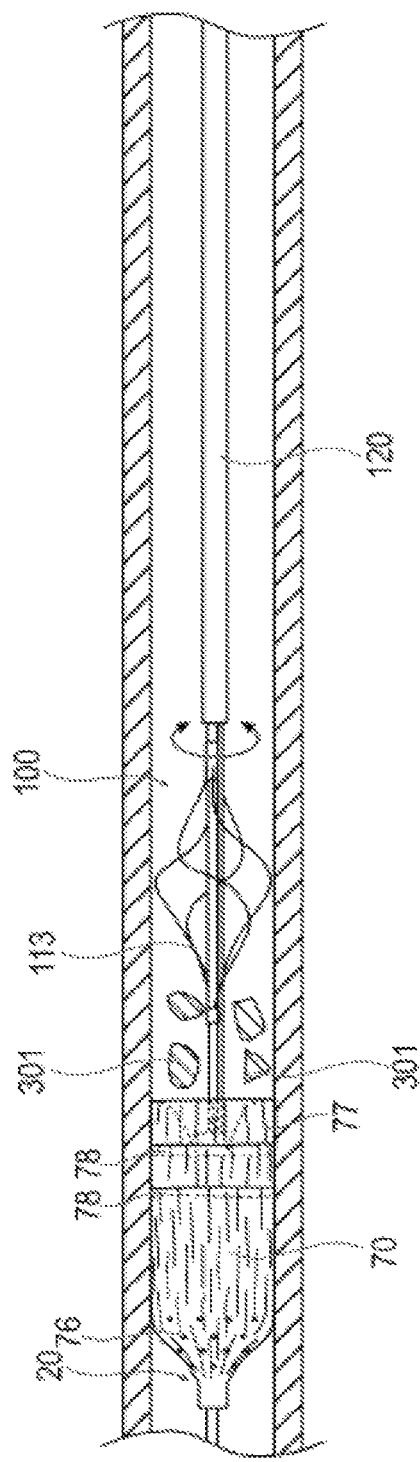
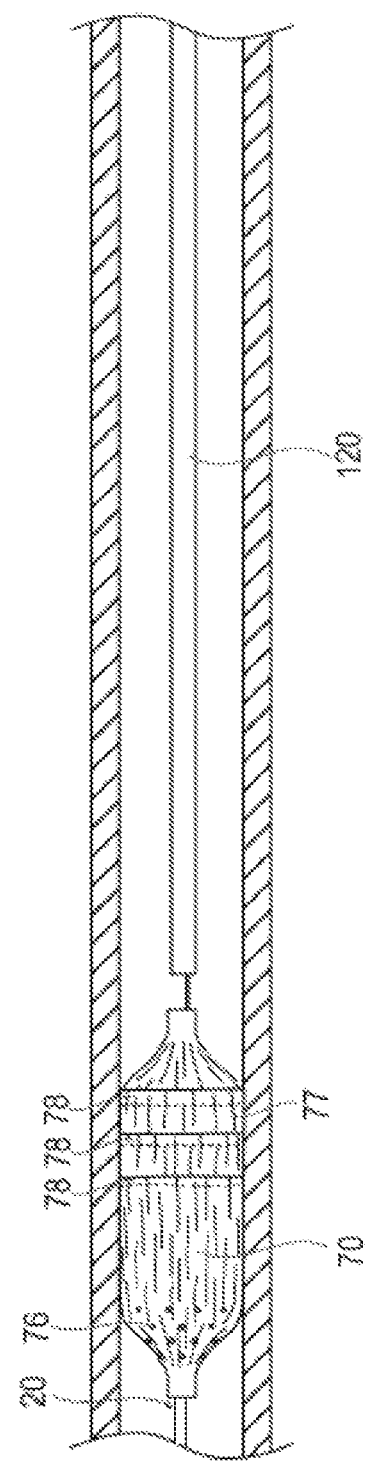
FIG. 21A
FIG. 21B

FIG.25A
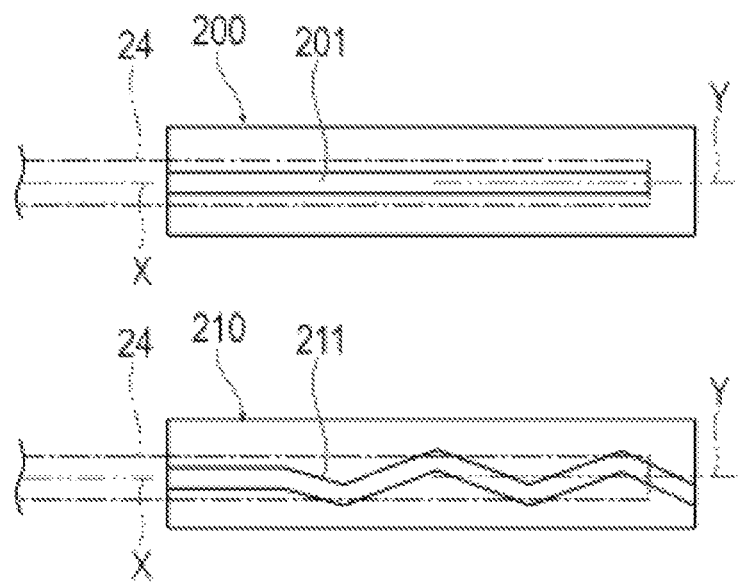
FIG.25B
FIG.26
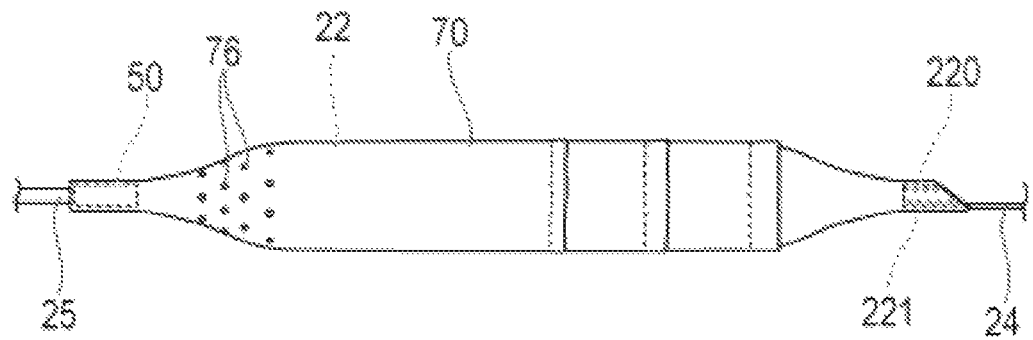

MEDICAL DEVICE AND METHOD FOR TREATMENT

CROSS-REFERENCE TO RELATED APPLICATION

This application claims priority to Japanese Application No. 2016-031782 filed on Feb. 23, 2016, the entire content of which is incorporated herein by reference.

TECHNICAL FIELD

The present disclosure relates to a medical device to be inserted into a lumen of a living body and a method for treatment with the medical device.

BACKGROUND DISCUSSION

There occasionally arises pains or tumors when a vein is partly clogged with a thrombus or the like. One method of treatment for such troubles is by the removal of thrombi through a thrombus-removing device which is inserted percutaneously. This method, however, involves a possibility of causing pulmonary embolism in the case where the thrombus which has entirely or partly peeled off a blood vessel wall reaches a lung together with blood flow. A common countermeasure to avoid this trouble is to use a thrombolytic agent before and after treatment and/or during treatment, or to remove by suction as many thrombi as possible during treatment. Such measures, however, still have the possibility that some peeled thrombi large enough to cause clinical problems reach the lung.

One of the known methods for avoiding pulmonary embolism involves the use of a filter to catch and collect thrombi flowing through the blood vessel. For example, U.S. Pat. No. 6,142,987 discloses a device which is composed of a long wire and a reticulate filter attached to the distal part of the wire, with the wire laying at the center of the filter.

Unfortunately, the wire is positioned along the center axis of the filer and hence the filter is liable to turn around the wire. This is true particularly in the case where a device is inserted into the blood vessel along the wire and the device is turned, the wire receives a revolving force, thereby causing the filter to turn. The result of the filter turning is a decrease in the filter's ability to catch thrombi and the like in the blood vessel. This in turn leads to an increased burden on the living body.

SUMMARY

The disclosure herein provides a medical device and a method for treatment with the medical device, the medical device being able to suppress the decrease of its function in the lumen of the living body and the method being practicable without increase in burden on the living body.

The present disclosure is directed to a medical device which is designed to be inserted into a lumen of a living body, the medical device including a long shaft part and a cylindrical hollow body which is arranged at a distal part of the shaft part and which has a lumen into which a guide wire is inserted. The shaft part has a center axis at a position which differs from a center axis of the hollow body on the cross section perpendicular to the center axis of the shaft part. The hollow body has a housing part extending along the center axis of the hollow body, the hollow body being a groove depressed from an outer peripheral surface to an inner peripheral surface or a slit penetrating from an outer peripheral surface to an inner peripheral surface. The shaft part is positioned between inner surfaces facing from the outer peripheral surface to the inner peripheral surface in such a way that at least a part of the shaft part constitutes the slit or the groove of the housing part.

A further aspect of the disclosure is directed to a method for performing treatment by inserting the medical device defined above into a lumen of a living body. The method includes: a step of inserting a distal part of the medical device into the lumen of the living body, a step of inserting a long tubular body along the shaft part into the lumen of the living body, a step of rotating the shaft part relative to the tubular body and adjusting a position in a rotating direction of the shaft part, a step of housing the medical device in the tubular body, and a step of pulling out the medical device from the lumen of the living body.

Thus configured, the medical device and the method for treatment with the medical device produce the following effects. Since the center axis of the shaft part does not coincide with the center axis of the hollow body, the shaft part is less liable to turn than in the case where the center axis of the shaft part coincides with the center axis of the hollow body. This prevents the device from becoming poor in performance in the lumen of the living body, and thus leads to a reduction of burden for the living body. In addition, due to the fact that a housing part for the hollow body is formed along the center axis of the hollow body permits the shaft part to be arranged easily along the hollow body even though the shaft part is set off from the center axis of the hollow body.

BRIEF DESCRIPTION OF THE DRAWINGS

FIG. 1 is a plan view illustrating the medical device according to an exemplary embodiment of the disclosure;

FIG. 2 is a plan view illustrating the medical device according to the exemplary embodiment, the medical device being composed of an expanding tool, a pressing shaft, and a sheath, which are combined together;

FIGS. 3A and 3B are plan views illustrating a covering part of the expanding tool, wherein FIG. 3A illustrates the covering part in its expanded state, and FIG. 3B illustrates the covering part in its contracted state;

FIGS. 4A and 4B are plan views illustrating an expandable part in the covering part of the expanding tool, wherein FIG. 4A illustrates the expandable part in its expanded state, and FIG. 4B illustrates the expandable part in its contracted state;

FIGS. 9A and 9B are sectional views illustrating the joined shaft part and the inner tube, wherein FIG. 9A is a sectional view taken along the line B-B in FIG. 8, and FIG. 9B is a sectional view taken along the line C-C in FIG. 8;

FIGS. 14A and 14B are sectional views illustrating a state in the blood vessel, wherein FIG. 14A illustrates the medical device inserted into the blood vessel, and FIG. 14B illustrates the medical device, with the distal part of the expandable part and the covering part expanded in the blood vessel;

FIGS. 15A and 15B are sectional views illustrating the state in the blood vessel, wherein FIG. 15A illustrates the medical device, with the expanding tool dwelling in the blood vessel, and FIG. 15B illustrates the medical device, with the removing device inserted into the blood vessel;

FIGS. 16A and 16B are sectional views illustrating the state in the blood vessel, wherein FIG. 16A illustrates the medical device, with a stirring part of the removing device expanded, and FIG. 16B illustrates how the expanded stirring part has crushed a thrombus or the like;

FIGS. 21A and 21B are sectional views illustrating the state in the blood vessel, wherein FIG. 21A illustrates the state in which the thrombus sticking to the expanding tool is being suctioned, and FIG. 21B illustrates the state in which the stirring part is housed into an outermost sheath;

FIGS. 22A and 22B are sectional views illustrating the state in the blood vessel, wherein FIG. 22A illustrates the state in which the removing device has been pulled out of the blood vessel, and FIG. 22B illustrates the state in which the covering part and the expandable part have been housed into the sheath;

FIGS. 23A and 23B are sectional views illustrating the state in the blood vessel, wherein FIG. 23A illustrates the state in which a center axis of the expandable part has been brought close to the center axis of the sheath, and FIG. 23B illustrates the state in which the center axis of the expandable part has been taken away from the center axis of the sheath;

FIGS. 24A and 24B are sectional views illustrating how the removing device works before and after the expanding tool is moved in the blood vessel, wherein FIG. 24A illustrates a working position of the removing device before the movement of the expanding tool, and FIG. 24B illustrates the working position of the removing device after the movement of the expanding tool;

FIGS. 25A and 25B are plan views illustrating the inner tube of the expanding tool according to modified examples of the exemplary embodiment, wherein FIG. 25A illustrates a first modified example, and FIG. 25B illustrates a second modified example;

FIG. 26 is a plan view illustrating the expandable part and the covering part of the expanding tool according to another modified example;

DETAILED DESCRIPTION

Figure 5:
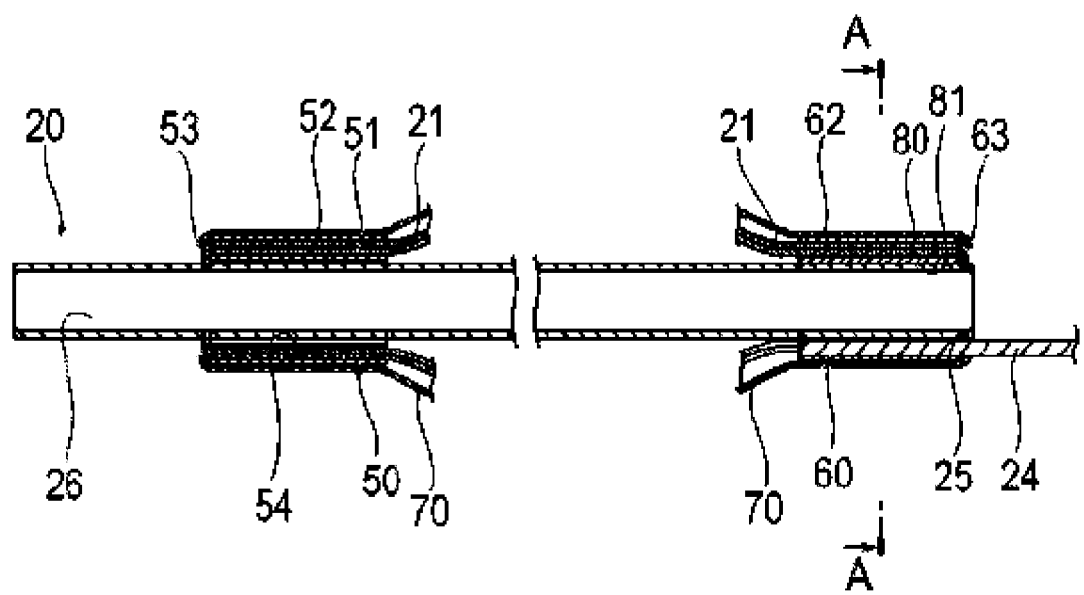
FIG. 5 is an enlarged sectional view illustrating a proximal side connecting part and a distal side connecting part of the medical device according to an exemplary embodiment.

An exemplary embodiment of the disclosure herein will be described below with reference to the accompanying drawings. The scale of the drawings here may occasionally be different from the actual one because it is exaggerated for the sake of explanation.

A medical device 10 according to an exemplary embodiment of the disclosure is used to control the flow in a blood vessel so as to remove any object, such as thrombus and plaque, from the blood vessel by suction. The following terms are used in this specification: "distal side" to denote a side of the medical device from which the blood vessel is inserted; and "proximal side" to denote a side of the medical device at which the medical device is manipulated. Moreover, the objects to be removed are not necessarily restricted to thrombus and plaque but they include any object which may exist in the lumen of the living body. Also, the following terms are used in this specification: "upstream side" to denote a side of the blood vessel from which the blood flows; and "downstream side" to denote a side of the blood vessel to which the blood flows.

The medical device 10 according to the exemplary embodiment of the present disclosure includes an expanding tool 20 which blocks the flow of blood in the blood vessel, a sheath 30 which houses the expanding tool 20 therein, and a pressing shaft 40 which pushes out the expanding tool 20 from the sheath 30, as illustrated in FIGS. 1 and 2. Incidentally, the blocking of blood flow is accomplished by closing or diminishing the cross section perpendicular to the axis of the blood vessel. Therefore, the term "blocking" means controlling or suppressing (shutting off or reducing) of the blood flow.

The expanding tool 20 includes: an expandable part 22 which is a reticulate cylindrical body capable of elastic deformation and has a plurality of pores 21A; a covering part 70 which surrounds the outer periphery of the expandable part 22; a long shaft part 24 connected to the proximal part of the expandable part 22; and a tubular body 25 for guide wire, which passes through the expandable part 22 and the covering part 70, as illustrated in FIGS. 3A, 3B, 4A, and 4B.

As illustrated in FIGS. 1, 2, 5, and 6, the shaft part 24 is a wire which extends from the handle to the expandable part 22. The tubular body 25 for guide wire passes through the expandable part 22 and the covering part 70, so that a guide wire lumen 26 is formed therein. Also, the tubular body 25 for guide wire is formed such that its outer peripheral surface of the proximal part is fixed to an inner peripheral surface 81 of an inner tube 80 (hollow body) which is provided at the proximal part of the expandable part 22.

The shaft part 24 may be suitably formed from any material, such as stainless steel and shape-memory alloy, without specific restrictions. The tubular body 25 for guide wire may be suitably formed from any material, including: plastics such as polyimide and polyamide; stainless steel; and shape-memory alloy, without specific restrictions.

As illustrated in FIGS. 4A and 4B, the expandable part 22 includes a plurality of flexible and deformable wires 21 which are reticulatly braided to form a cylindrical body having the pores 21A. The expandable part 22 also includes a distal side connecting part 50 which is rigidly connected to the tubular body 25 for guide wire, and a proximal side connecting part 60 which is slidably connected to the tubular body 25 for guide wire. The proximal side connecting part 60 is constructed such that the inner peripheral surface 81 of the inner tube 80 is fixed to the outer peripheral surface of the tubular body 25 for guide wire. The distal side connecting part 50 is constructed such that an inner peripheral surface 54 of an inner tube 51 is slidable along the outer peripheral surface of the tubular body 25 for guide wire. The wires 21 are so braided as to form a tubular body which has the pores 21A between the wires 21 adjacent to each other.

The expandable part 22 is capable of deformation in its natural state without external force acting thereon. That is, it takes on an expanded state with its diameter increased due to its own elastic force (restoring force) of the wires as illustrated in FIG. 4A; it also takes on a contracted state with its outer diameter decreased due to elastic deformation as illustrated in FIG. 4B. The expandable part 22 includes a proximal side tapered part 22A, an expandable part central part 22B, and a distal side tapered part 22C. The proximal side tapered part 22A has inner and outer diameters gradually increasing in going from the proximal part to the distal side. The expandable part central part 22B is positioned at the distal side of the proximal side tapered part 22A and has an approximately constant outer diameter. The distal side tapered part 22C has inner and outer diameters gradually decreasing in going from the expandable part central part 22B to the distal side. The expandable part central part 22B is a site which expands to press the covering part 70 against the inner wall of the blood vessel. When the expandable part 22 is not covered with the covering part 70, the expandable part 22 expands due to its own expanding force and has a maximum outer diameter which is larger than the maximum inner diameter of the covering part 70.

Figure 6:
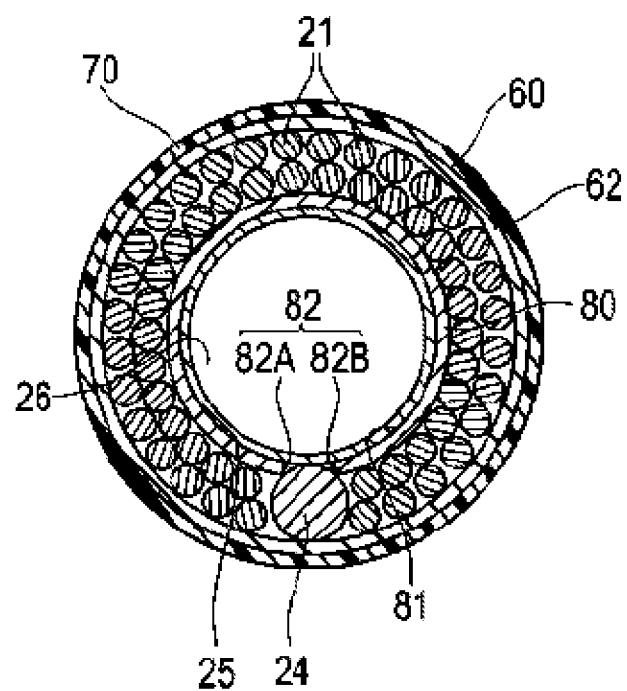
FIG. 6 is a sectional view taken along the line A-A in FIG. 5.
Figure 7:
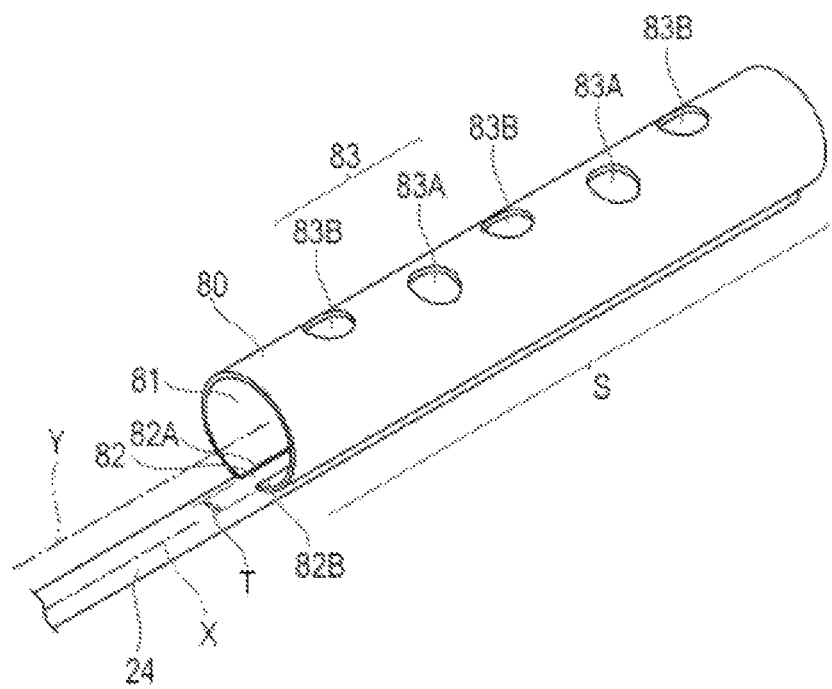
FIG. 7 is a perspective view illustrating a joined shaft part and an inner tube of the medical device according to the exemplary embodiment.
Figure 8:
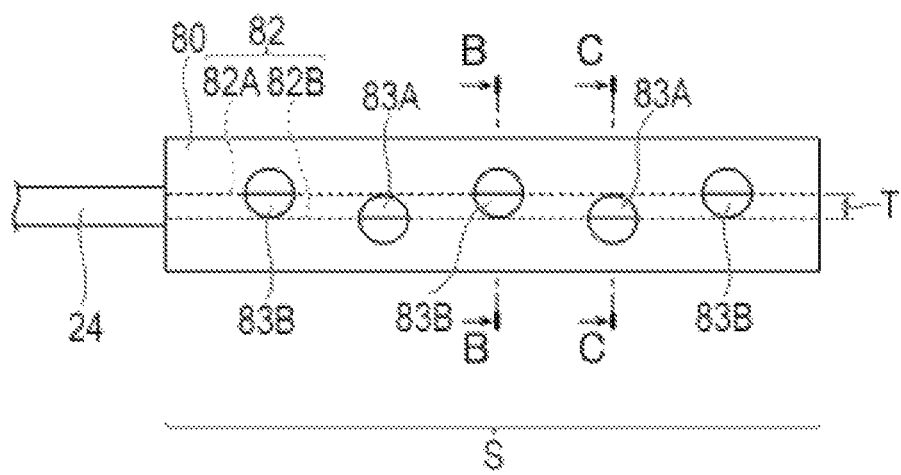
FIG. 8 is a plan view illustrating the joined shaft part and the inner tube.

The proximal side connecting part 60 includes an inner tube 80 positioned inside the wires 21, an outer tube 62 (outside hollow body) positioned outside the wires 21, and a joining part 63 which joins together the inner tube 80 and the outer tube 62 at their end parts, as illustrated in FIGS. 5 and 6. The proximal side end part of the wires 21 and the distal part of the shaft part 24 are sandwiched and fixed between the inner tube 80 and the outer tube 62. The outer tube 62 takes on a cylindrical shape and the inner tube 80 having a cylindrical shape has a slit 82 as a housing part. The proximal side connecting part 60 is constructed such that the internal peripheral surface 81 of the inner tube 80 is firmly fixed to the external peripheral surface of the tubular body 25 for guide wire. The joining part 63 may be omitted in the case where the wires 21 can be fixed.

The inner tube 80 and the shaft part 24 are joined together in advance by laser welding, as illustrated in FIGS. 7 to 10. This structure permits the wires 21 to be easily confined between the inner tube 80 and the outer tube 62 in the subsequent steps, thereby contributing to improved operability. A center axis X of the shaft part 24 is positioned parallel to and apart from a center axis Y of the inner tube 80, at least within a range S over which the center axis X is juxtaposed with the inner tube 80 in the axial direction.

The inner tube 80 is a tubular body which has a uniform inner diameter and outer diameter in the axial direction. The inner tube 80 includes: the slit 82 which penetrates the inner tube 80 from the internal peripheral surface to the external peripheral surface of the inner tube 80 and which extends from the distal side end part to the proximal side end part; and a plurality of opening parts 83 which penetrate from the external peripheral surface to the internal peripheral surface of the inner tube 80 at positions different from the position of the slit 82. The outer peripheral surface of the inner tube 80 is the outside surface which faces outward in the radial direction and which comes into contact with the wires 21. The inner peripheral surface of the inner tube 80 is the inside surface which faces inward in the radial direction and which comes into contact with the tubular body 25 for guide wire. Incidentally, the slit 82 may extend from the position between the distal side end part and the proximal side end part to the proximal side end part. The slit 82 is formed parallel to the center axis Y of the inner tube 80. The slit 82 has a first slit inner surface 82A (inner surface) and a second slit inner surface 82B (inner surface) which face each other and are symmetrically aligned with each other. The inner tube 80 is constructed such that an approximately right angle 87 is formed between the first slit inner surface 82A and the external peripheral surface and between the second slit inner surface 82B and the external peripheral surface. However, the angle 87 does not necessarily need to be a right angle. In addition, the angle 87 may be so formed as to have a curvature. A distance T (width) between the first slit inner surface 82A and the second slit inner surface 82B is uniform along the center axis X. The distance T is not larger than the diameter of the shaft part 24, according to the exemplary embodiment of the present disclosure. This produces the following effect. The outer peripheral surface of the shaft part 24 comes into contact with both the first slit inner surface 82A and the second slit inner surface 82B from the outside in the radial direction, and the inner tube 80 and the shaft part 24 are accurately positioned so that the center axis X and the center axis Y are parallel to each other. Thus, the shaft part 24 is at least partly positioned between the first slit inner surface 82A and the second slit inner surface 82B from the outside in the radial direction. Accordingly, the inside of the inner tube 80 is secured as a space into which a guide wire 90 is inserted, as illustrated in FIG. 6. The shaft part 24 can be compactly housed together with the wires 21 between the inner tube 80 and the outer tube 62. In addition, the fact that the shaft part 24 is partly positioned between the first slit inner surface 82A and the second slit inner surface 82B produces the effect of minimizing, as much as possible, the outer diameter and inner diameter of the outer tube 62 and hence minimizing, as much as possible, the inner and outer diameters of the sheath 30 that can be inserted. Incidentally, the distance T may be smaller than the diameter of the shaft part 24.

The shaft part 24 is positioned such that the center axis X thereof is arranged between the first slit inner surface 82A and the second slit inner surface 82B of the inner tube 80. Alternatively, the shaft part 24 is positioned such that the center axis X thereof is arranged outside in the radial direction with respect to the outer peripheral surface of the inner tube 80.

In addition, the shaft part 24 is positioned such that when the outer peripheral surface of the shaft part 24 comes into contact with both the first slit inner surface 82A and the second slit inner surface 82B from outside in the radial direction, a space is formed between the outer peripheral surface of the shaft part 24 and both the first slit inner surface 82A and the second slit inner surface 82B. This space prevents the molten metal produced during the welding from swelling on the inner peripheral surface of the inner tube 80, which contributes to the smooth insertion of the guide wire.

Figure 10:
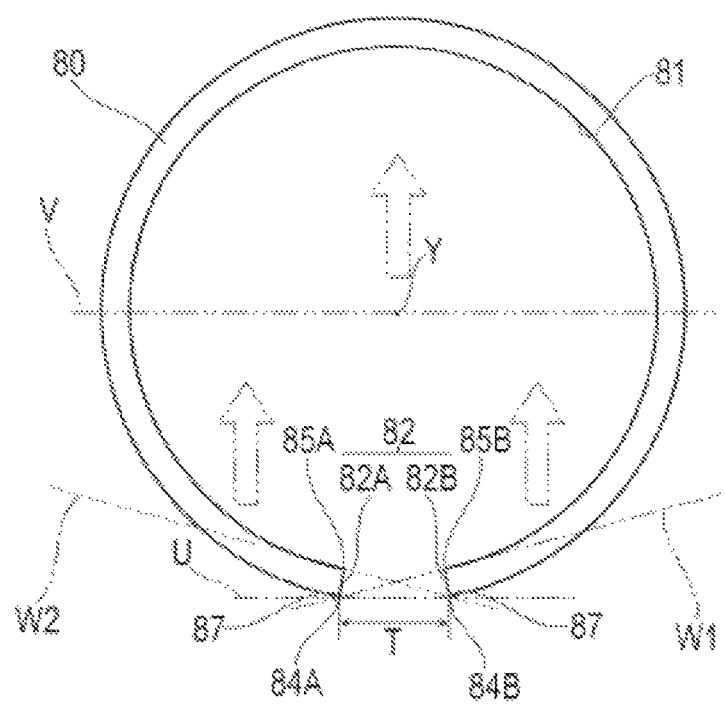
FIG. 10 is a plan view illustrating the inner tube as viewed in its axial direction.

As illustrated in FIG. 10, the first slit inner surface 82A has a first slit outer edge part 84A which borders on the outer peripheral surface of the inner tube 80 and also has a first slit inner edge part 85A which borders on the internal peripheral surface of the inner tube 80. In addition, the second slit inner surface 82B has a second slit outer edge part 84B which borders on the external peripheral surface of the inner tube 80 and also has a second slit inner edge part 85B which borders on the internal peripheral surface of the inner tube 80. The shaft part 24 is in contact with the first slit outer edge part 84A and the second slit outer edge part 84B, so that it is accurately positioned relative to the inner tube 80. The inner tube 80 and the shaft part 24 are joined together along the first slit outer edge part 84A and the second slit outer edge part 84B.

Figures 9A, 9B:
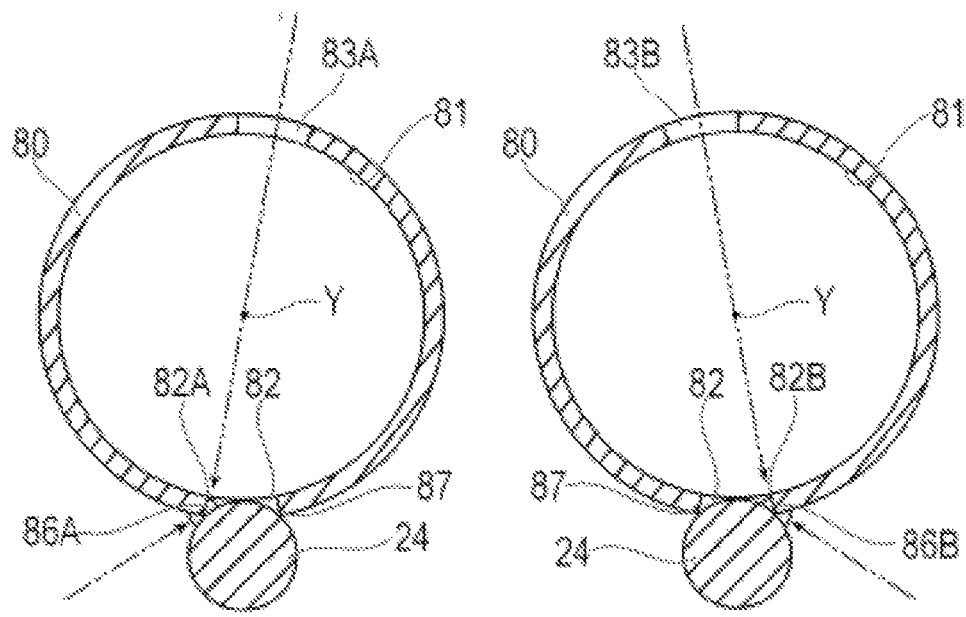

As illustrated in FIGS. 9A and 9B, a first jointing part 86A is formed on the first slit inner surface 82A by being joined to the shaft part 24 by laser welding, and a second jointing part 86B is formed on the second slit inner surface 82B by being joined to the shaft part 24. The first jointing part 86A results from laser-welding achieved by a laser beam coming through a first opening part 83A which is positioned opposite to the first slit inner surface 82A with respect to the center axis Y. The laser-welding is also achieved by a laser beam coming from outside of the inner tube 80 in the radial direction (see the two-dot chain line in FIG. 9A). The laser-welding by means of two laser beams coming from the inside and the outside of the inner tube 80 ensures a strong jointing between the inner tube 80 and the shaft part 24. Since the inner tube 80 is provided with the first opening part 83A and the slit 82, it is possible to easily weld the first slit outer edge part 84A to the shaft part 24 by welding work which is performed from the inner peripheral surface side.

The first opening part 83A is positioned on an imaginary extension line connecting the first slit inner edge part 85A and the first slit outer edge part 84A. A second opening part 83B is positioned on an imaginary extension line connecting the second slit inner edge part 85B and the second slit outer edge part 84B.

The second jointing part 86B results from laser-welding achieved by a laser beam coming through the second opening part 83B which is positioned opposite to the second slit inner surface 82B with respect to the center axis Y. The laser-welding is also achieved by a laser beam coming from outside of the inner tube 80 in the radial direction (see the two-dot chain line in FIG. 9B). The laser-welding by means of two laser beams coming from the inside and the outside of the inner tube 80 ensures a strong jointing between the inner tube 80 and the shaft part 24. Since the inner tube 80 is provided with the second opening part 83B and the slit 82, it is possible to easily weld the second slit outer edge part 84B to the shaft part 24 by welding work which is performed from the inner peripheral surface side. According to this exemplary embodiment, there are three second opening parts 83B and there are two first opening parts 83A, each of which is held between two of the second opening part 83B. The number and arrangement of these opening parts are not restricted to those mentioned above. Incidentally, the first and second opening parts may be omitted.

It is not always necessary that the first opening part 83A and the second opening part 83B are positioned respectively opposite the first slit inner surface 82A and the second slit inner surface 82B with respect to the center axis Y. For example, as illustrated in FIG. 10, the first opening part 83A and the second opening part 83B are positioned opposite to the side of the slit 82 relative to a center plane V on which the center axis Y is positioned, the center plane V being parallel to a plane U on which both the first slit outer edge part 84A and the second slit outer edge part 84B are positioned. Despite this structure, it is possible to perform welding to the shaft part 24 by irradiation with a laser beam to the first slit inner surface 82A and the second slit inner surface 82B through the first opening part and the second opening part. Moreover, the first opening part and the second opening part may be positioned on the side of the center axis Y with respect to a plane W1 on which both the first slit outer edge part 84A and the second slit inner edge part 85B are positioned, and on the side of the center axis Y with respect to a plane W2 on which both the second slit outer edge part 84B and the first slit inner edge part 85A are positioned. Despite this structure, it is possible to perform welding to the shaft part 24 by irradiation with a laser beam to the first slit inner surface 82A and the second slit inner surface 82B through the first opening part and the second opening part. Further, the inner tube (hollow body) 80 may have a cross section across the center axis Y, whose shape is not only circular but also elliptical or polygonal.

According to the exemplary embodiment, the center axis Y is positioned on the extension line connecting the first slit inner edge part 85A and the first slit outer edge part 84A; however, this is not necessarily the case. Moreover, the center axis Y is positioned on the extension line connecting the second slit inner edge part 85B and the second slit outer edge part 84B; however, this is not necessarily the case. Therefore, for example, the first slit inner surface 82A and the second slit inner surface 82B may be parallel to each other. In addition, the first slit inner surface 82A and the second slit inner surface 82B may be a certain distance apart from each other, the distance increasing in going from the outer peripheral surface of the inner tube 80 to the inner peripheral surface of the inner tube 80.

As illustrated in FIG. 5, the distal side connecting part 50 includes the inner tube 51 positioned inside the wires 21, an outer tube 52 positioned outside the wires 21, and a joining part 53 joining together the inner tube 51 and the outer tube 52 at their end parts. The distal side end part of the wires 21 is sandwiched and fixed between the inner tube 51 and the outer tube 52. The inner tube 51 and the outer tube 52 are cylindrical and coaxially arranged. The distal side connecting part 50 is movable in the axial direction relative to the tubular body 25 for guide wire because the tubular body 25 for guide wire is slidably inserted in the inner tube 51 such that there exists a gap between the inner tube 51 and the tubular body 25 for guide wire. Also, the joining part 53 may be omitted so long as the wires 21 can be fixed. The gap between the inner tube 51 and the tubular body 25 for guide wire is not specifically restricted; however, it should preferably range from 0.01 to 1.0 mm.

The distal side connecting part 50 slides toward the proximal side and approaches the proximal side connecting part 60 along the tubular body 25 for guide wire as the expandable part 22 expands, as illustrated in FIGS. 3A and 4A. Also, the distal side connecting part 50 slides toward the distal side and recedes from the proximal side connecting part 60 along the tubular body 25 for guide wire as the expandable part 22 contracts, as illustrated in FIGS. 3B and 4B. Since the distal side connecting part 50 approaches or recedes from the proximal side connecting part 60, the braided expandable part 22 can vary in its outer diameter.

The wires 21 are not specifically restricted in number. An adequate number may range from 4 to 72, for example. Moreover, the wires 21 may be formed by braiding under any condition without specific restrictions, or other types of interweaving.

The wires 21 are not specifically restricted in outer diameter. An adequate outer diameter may range from 20 to 300 μm, for example, depending on the material of the wires 21 and the use of the expandable part 22.

The wires 21 should preferably be made of any one of the flexible materials including: shape-memory alloy which is given the shape-memory effect or superelasticity upon heat treatment; stainless steel; tantalum (Ta); titanium (Ti); platinum (Pt); gold (Au); tungsten (W); polyolefin such as polyethylene and polypropylene; polyamide; polyester such as polyethylene terephthalate; fluorine polymer such as tetrafluoroethylene-ethylene copolymer (ETFE); polyether ether ketone (PEEK); and polyimide. Preferable shape-memory alloys include Ni—Ti alloys, Cu—Al—Ni alloys, and Cu—Zn—Al alloys, which may be used in combination with one another. The structures in which a plurality of materials are used in combination with one another include the structure in which the core wire of Pt for imparting radiopacity is coated with Ni—Ti alloy, or the core wire of Ni—Ti alloy is coated with gold plating.

The outer tubes 52 and 62 are not specifically restricted in outer diameter. For example, typical values range from 0.3 to 3.0 mm. The inner tubes 51 and 80 are also not specifically restricted in inner diameter. Typical values range from 0.1 to 2.0 mm, for example.

The inner tubes 51 and 80 and the outer tubes 52 and 62 may be formed from any material without specific restrictions. Preferable materials include stainless steel and shape-memory alloy.

The expandable part 22 may have a maximum outer diameter to be appropriately selected according to the inner diameter of the blood vessel to which the medical device is applied. For example, typical values range from 1 to 40 mm. The expandable part 22 in its contracted state may have an outer diameter to be properly selected according to the inner diameter of the blood vessel to which the medical device is applied. Typical values range from 0.3 to 4.0 mm, for example. The expandable part 22 in its contracted state may have a length in the axial direction to be adequately selected according to the blood vessel to which the medical device is applied. Typical values range from 20 to 150 mm, for example.

The covering part 70 is a tubular member which is formed from a thin film so as to cover the outer periphery of the expandable part 22 as a whole, as illustrated in FIGS. 3A and 3B.

As illustrated in FIGS. 1 and 2, the sheath 30 includes a sheath tubular body 31, a hub 32, and a kink-resistant protector 33. The sheath tubular body 31 has a lumen 34 in which the expanding tool 20 is housed, and opens at a tubular body opening part 36 which is formed at the distal side end part of the sheath tubular body 31. The hub 32 is fixed to the proximal side end part of the sheath tubular body 31, and has the hub opening part 35 communicating with the lumen 34. The kink-resistant protector 33 is a flexible member that covers the sheath tubular body 31 and the connecting site of the hub 32. The kink-resistant protector 33 protects the sheath tubular body 31 from kinking.

The sheath tubular body 31 may be formed from any material without specific restrictions. Typical examples suitably used include: polyolefins such as polyethylene, polypropylene, ethylene-propylene copolymer, and ethylene-vinyl acetate copolymer; polyvinyl chloride; polystyrene; polyamide; polyimide; and a combination thereof. The sheath tubular body 31 may be formed from more than one material or may have a reinforcing material such as wire embedded therein.

The pressing shaft 40 is a tubular body housed in the lumen 34 of the sheath 30. The pressing shaft 40 has a pushing lumen 41 formed therein into which the shaft part 24 of the expanding tool 20 is inserted. The pushing lumen 41 has an inner diameter which is smaller than the outer diameter of the proximal side connecting part 60 of the expanding tool 20. Therefore, the proximal side connecting part 60 cannot enter the pushing lumen 41, and hence this permits the pressing shaft 40 to push the proximal side connecting part 60 toward the distal side.

The following description is concerned with a removing device 100 for removing thrombi by insertion into the blood vessel.

Figure 11:
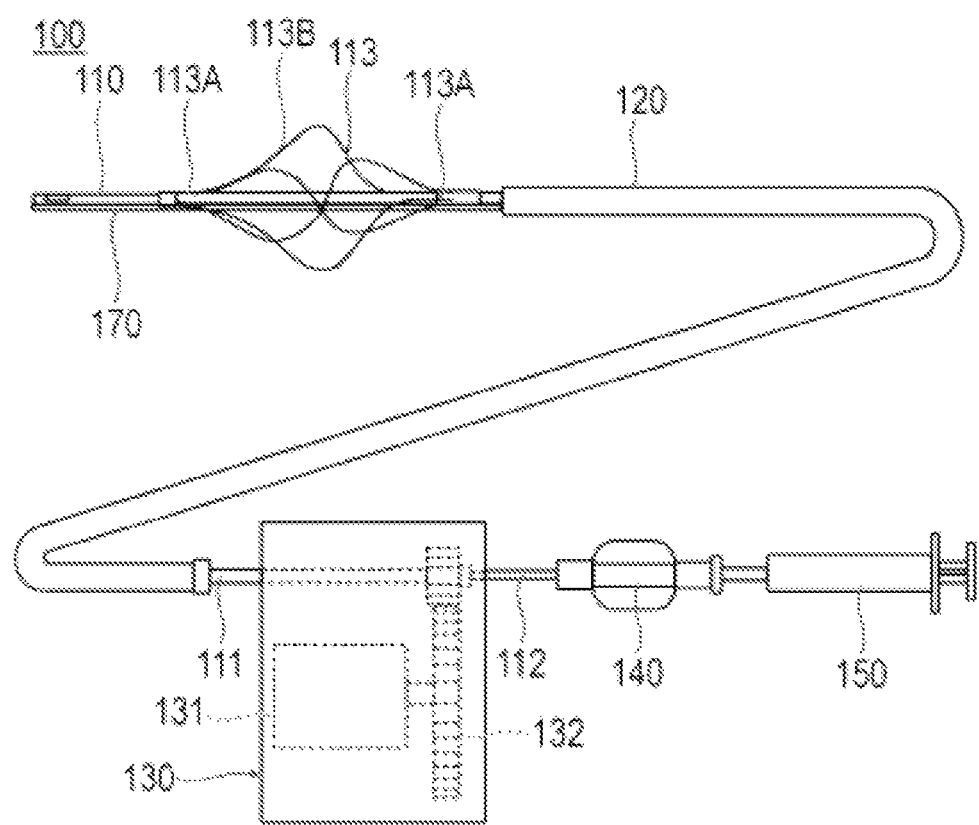
FIG. 11 is a plan view illustrating a removing device according to an exemplary embodiment of the disclosure.
Figure 12:
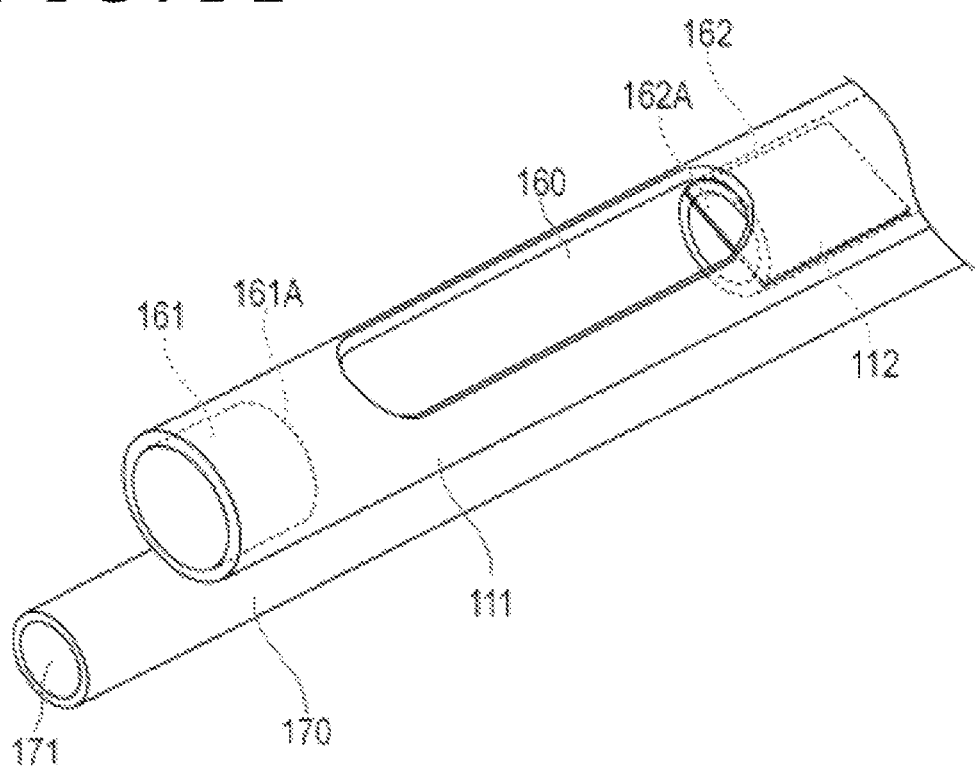
FIG. 12 is a perspective view illustrating a distal part of the removing device.
Figure 13:
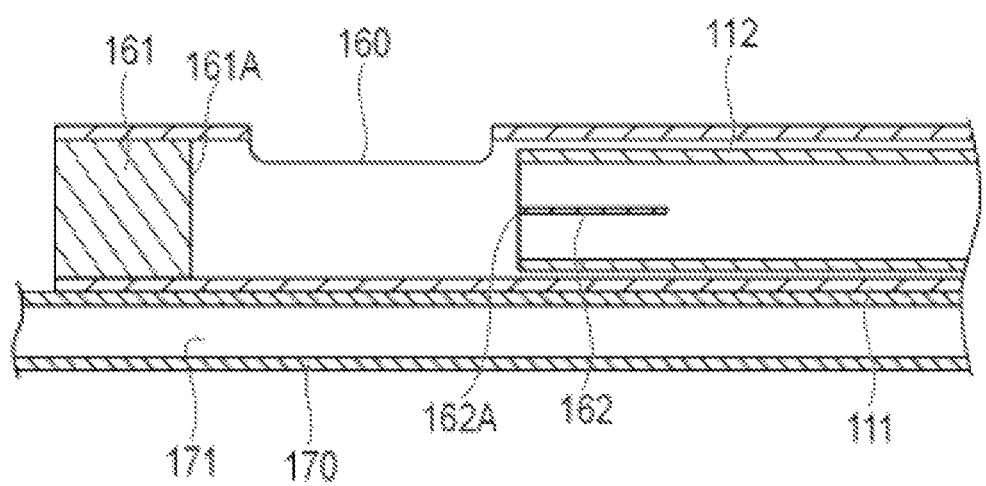
FIG. 13 is a sectional view illustrating the distal part of the removing device.

As illustrated in FIGS. 11 to 13, the removing device 100 includes: a shaft main body 110 formed long; an outermost sheath body 120 for housing therein the shaft main body 110 and slidable in the axial direction relative to the shaft main body 110; and a tubular body 170 for guide wire, in which a second guide wire lumen 171 is formed. The removing device 100 additionally has a rotary drive unit 130 which rotates the shaft main body 110, a hub 140 provided at the proximal side end part of the shaft main body 110, and a syringe 150 coupled to the proximal side of the hub 140.

The shaft main body 110 is composed of a shaft outer tube 111 and a shaft inner tube 112, which are long and hollow. The shaft outer tube 111 and the shaft inner tube 112 have their respective inner lumens. The inner diameter of the shaft outer tube 111 is larger than the outer diameter of the shaft inner tube 112, so that the shaft inner tube 112 is housed in the hollow part of the shaft outer tube 111. The shaft inner tube 112 is movable in the axial direction relative to the shaft outer tube 111.

The shaft outer tube 111 has a distal side end part at which is formed the distal part of the shaft main body 110, and also has a proximal side end part at which is positioned the rotary drive unit 130. The shaft inner tube 112 has a proximal side end part which extends toward the proximal side with respect to the proximal side end part of the shaft outer tube 111, and which is coupled to the hub 140. The syringe 150 coupled to the hub 140 evacuates the hollow part of the shaft inner tube 112 by suction to generate a negative pressure state.

The tubular body 170 for guide wire is arranged around and firmly fixed to the shaft outer tube 111 along the shaft outer tube 111. The tubular body 170 for guide wire has the second guide wire lumen 171 into which the guide wire is inserted.

The shaft outer tube 111 is made of a material which is flexible and capable of transmitting the rotating power acting on the proximal side to the distal side. The shaft inner tube 112 is made of a material which is flexible and capable of transmitting the reciprocating power acting on the proximal side to the distal side. For example, the shaft outer tube 111 and the shaft inner tube 112 may be formed from a multi-layered, such as three-layered, tubular body in coil shape wound in alternating directions, and made of: polyolefin such as polyethylene and polypropylene; polyamide; polyester such as polyethylene terephthalate; fluorine polymer such as ethylene-tetrafluoroethylene copolymer (ETFE); polyether ether ketone (PEEK); or polyimide; or a combination thereof. These materials may have a reinforcing member such as wires embedded therein.

The outermost sheath body 120 may be formed from any material without specific restrictions. Typical preferable examples suitably used include: polyolefin such as polyethylene and polypropylene; polyamide; polyester such as polyethylene terephthalate; fluorine polymer such as ethylene-tetrafluoroethylene copolymer (ETFE); polyether ether ketone (PEEK); and polyimide. It may also be formed from a plurality of materials combined together, or a material having a reinforcement such as wires embedded therein.

The shaft outer tube 111 is provided with a stirring part 113 at the distal part thereof. The stirring part 113 is connected to the periphery of the shaft outer tube 111 at two base parts 113A which are the proximal side and the distal side. The two base parts 113A are bridged by spiral parts 113b. Each of the spiral parts 113b is twisted in the identical direction to each other along the axial direction. Moreover, the spiral parts 113b are fixed at positions different to each other in the circumferential direction and bend to different directions along the axial direction. Consequently, the stirring part 113 as a whole is formed such that it uniformly bulges in the circumferential direction. When the shaft outer tube 111 rotates, the stirring part 113 also rotates with it, so that it crushes thrombi in the blood vessel or stirs crushed thrombi.

The spiral parts 113b of the stirring part 113 are formed from flexible thin metal wires. The stirring part 113 remains held inside the outermost sheath body 120 until the shaft main body 110 is inserted into the desired site. After the shaft main body 110 has been inserted into the desired site, the outermost sheath body 120 is slid to the proximal side, so that the stirring part 113 is exposed to the outside of the outermost sheath body 120 and expands as illustrated in FIG. 11. For this reason, the spiral parts 113b should preferably be formed from a shape-memory material. An adequate material for the spiral parts 113b is a shape-memory alloy which acquires shape-memory effect or super-elasticity upon heat treatment, or stainless steel. Preferable examples of the shape-memory alloy include those of Ni—Ti, Cu—Al—Ni, and Cu—Zn—Al, and a combination thereof.

The rotary drive unit 130 includes a drive motor 131 and a gear part 132 which allows the drive motor 131 to be linked with the shaft outer tube 111 of the shaft main body 110. The drive motor 131 rotates to turn the shaft outer tube 111 in its circumferential direction. According to the exemplary embodiment, the drive motor 131 rotates so as to turn the shaft outer tube 111 in its mutually opposite directions alternately along the circumferential direction. As the result of the shaft outer tube 111 turning in its mutually opposite directions alternately, the blood flow changes in its direction alternately.

The shaft outer tube 111 has an opening part 160 having an elongate hole shape in the axial direction, the opening part 160 being formed near the distal part of the shaft outer tube 111. This opening part permits the shaft outer tube 111 to communicate with the inside and outside. The shaft outer tube 111 has a cylindrical attachment part 161 at the distal part thereof so as to block the hollow part of the shaft outer tube 111 to close the distal part of the shaft outer tube 111. The attachment part 161 has an attachment face 161A as a proximal face thereof, the attachment face 161A facing a distal face of the shaft inner tube 112. The attachment face 161A is positioned at the distal side with respect to the distal side end part of the opening part 160 of the shaft outer tube 111. The attachment part 161 may be formed from stainless steel or the like.

The shaft inner tube 112 has a distal side end face which is positioned at the proximal side end part of the opening part 160 of the shaft outer tube 111 or the proximal side with respect to the proximal side end part of the opening part 160. A cutting part 162 is provided in the hollow part at the distal side end part of the shaft inner tube 112. The cutting part 162 is formed from a thin metal plate; it has a width equivalent to the diameter of the shaft inner tube 112. It also has a sharp blade 162A at the distal part thereof.

As illustrated in FIG. 12, the blade 162A is arranged such that there is no step between the distal side end face of the blade 162A and the distal side end face of the shaft inner tube 112. Therefore, as the distal face of the shaft inner tube 112 comes into contact with the attachment face 161A of the attachment part 161, the blade 162A also comes into contact with the attachment face 161A. The shaft inner tube 112 moves back and forth in the axial direction along the shaft outer tube 111 over a distance from at least the position illustrated in FIG. 13 to the position at which it comes into contact with the attachment face 161A of the attachment part 161. That distal part of the shaft inner tube 112 may be thinner than those parts other than the distal part of the shaft inner tube 112 (the thickness equivalent to difference between the outer diameter of the inner tube and the inner diameter of the inner tube), and it may be as thin as the blade 162A of the cutting part 162.

The shaft outer tube 111 and the shaft inner tube 112 are coaxially arranged, so that the shaft outer tube 111 can be rotated back and forth in the circumferential direction by the rotary drive unit 130. However, the shaft outer tube 111 may be one which rotates in one direction instead of the one which rotates back and forth. The cutting part 162 is arranged in such a way that it divides into two parts the sectional area of the hollow part of the shaft inner tube 112.

The following is a description of the method of using the medical device 10 and the removing device 100 according to the exemplary embodiment. The description illustrates the removal of thrombi by suction from the blood vessel.

In the first step, an introducer sheath (not shown) is inserted percutaneously into the blood vessel at the position upstream (proximal side) side of a thrombus 300 in the blood vessel. The introducer sheath permits a guide wire 90 to be inserted into the blood vessel. The guide wire 90 is advanced to the distal side of a thrombus 300.

In the second step illustrated in FIG. 2, the medical device 10 is prepared for use, with the sheath 30 housing therein the expanding tool 20 and the pressing shaft 40. The expandable part 22 is arranged at the position near the distal side end part of the sheath tubular body 31 of the sheath 30; it is constrained in the contracted state. The shaft part 24 projects toward the proximal side from the hub opening part 35 of the hub 32.

Figure 14A:
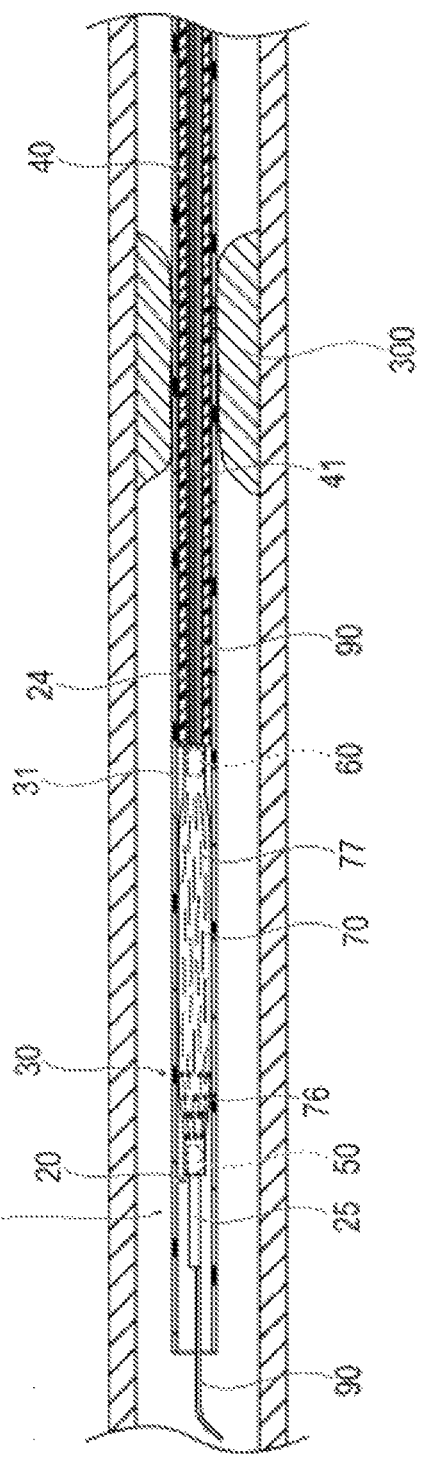

In the third step, the proximal side end part of the guide wire 90 which is positioned outside the patient's body is inserted into the guide wire lumen 26 of the medical device 10. As illustrated in FIG. 14A, the medical device 10 is advanced to the distal side of the thrombus 300 along the guide wire 90. To advance the guide wire 90 to the distal side of the thrombus 300, a support catheter that is separately provided may be used.

Figure 14B:
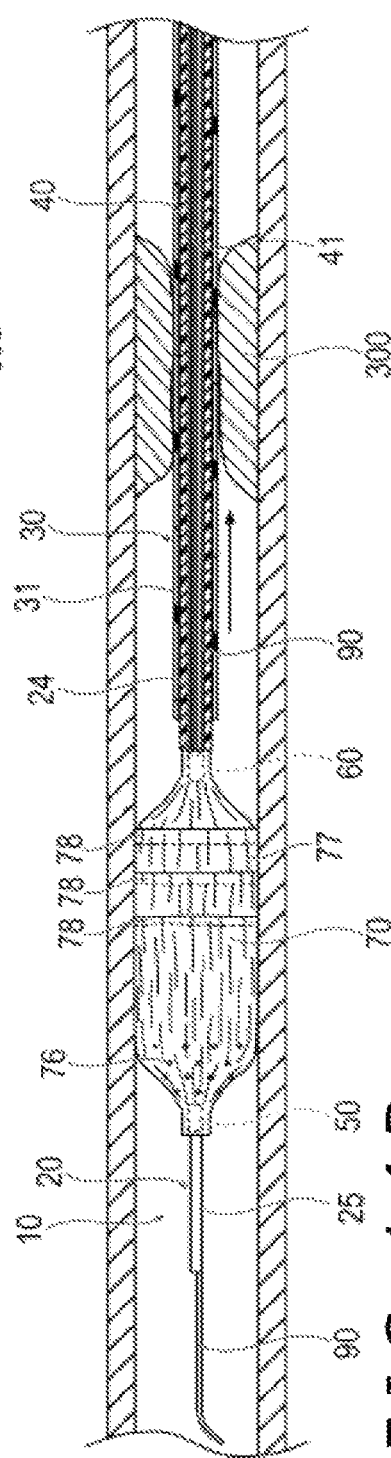

Subsequently, the sheath 30 is moved toward the proximal side, with the pressing shaft 40 kept immobile by holding with the hand. During this step, the distal side end part of the pressing shaft 40 comes into contact with the proximal side connecting part 60 or the proximal side end part of the tubular body 25 for guide wire. Because the expandable part 22 and the covering part 70 are kept immobile, it is possible to adjust as desired the positions of the expandable part 22 and the proximal part of the covering part 70 in the blood vessel. As the sheath 30 moves toward the proximal side relative to the pressing shaft 40, the expandable part 22 and the covering part 70 are released from the sheath tubular body 31. As the result, the distal side connecting part 50 approaches the proximal side connecting part 60, the expandable part 22 expands to an optimal size by its own restoring force, and the covering part 70 is pressed against the inner wall surface of the blood vessel and fixed thereto, as illustrated in FIG. 14B. Thus, the expandable part 22, which is formed in a mesh-like shape, can be firmly fixed, with the covering part 70 pressed into the inner wall surface of the blood vessel. The covering part 70 has folds 77 extended and spread by the expandable part 22 in conformity with the inner diameter and shape of the blood vessel and thus it is pressed against and brought into contact with the inner wall surface of the blood vessel by the expandable part 22. Further, the covering part 70 in contact with the inner wall surface of the blood vessel does not form any gap between it and the blood vessel even though the folds 77 partly remain because it is pressed against the inner wall surface of the blood vessel by the expandable part 22. In addition, since the expandable part 22 in its expanded state becomes shorter in the axial direction, the covering part 70 forms at least one overlapping part 78 in which overlapping takes place in the axial direction by utilizing the extra length in the axial direction in the expanded state.

Since the expandable part 22 is housed in the covering part 70 with its expanded diameter compulsorily limited by the covering part 70, it is firmly fixed to the inner wall surface of the blood vessel with a sufficient expanding force even when it has an expanded large outer diameter not only when it has an expanded small diameter. For this reason, the medical device can be applied to blood vessels broadly ranging in inner diameter.

Figure 15A:
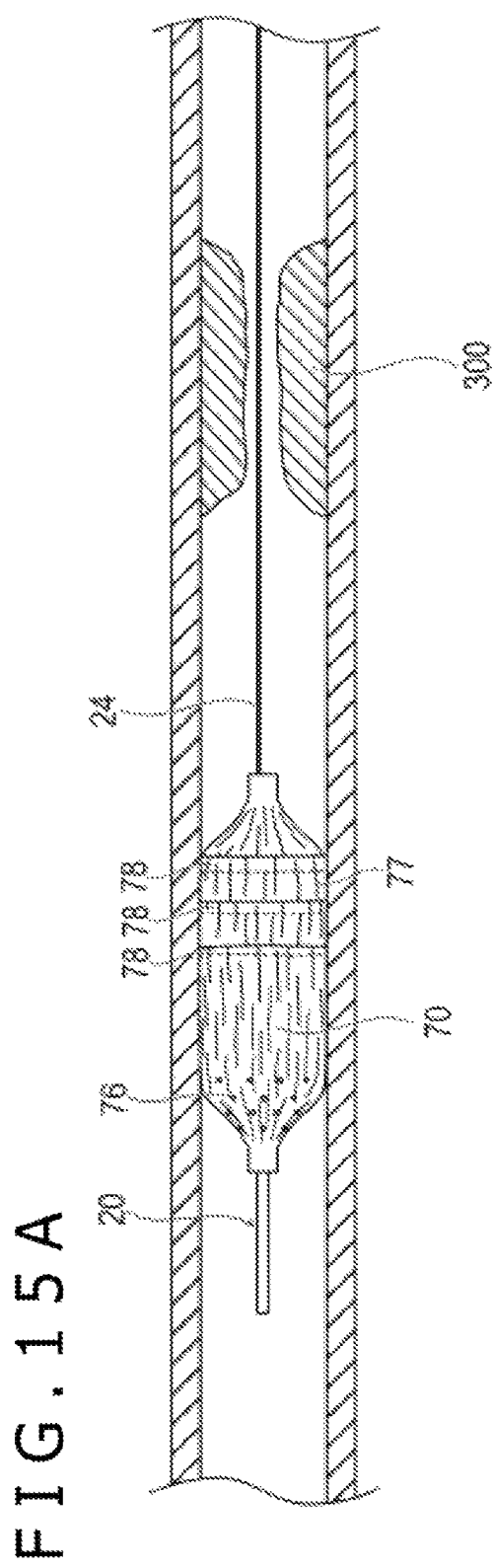

Since the maximum diameter to be achieved by expansion of the expandable part 22 is larger than the diameter of the blood vessel into which the expandable part 22 is inserted, the expandable part 22 does not expand completely inside the blood vessel but generates expanding force, thereby allowing the covering part 70 to effectively come into contact with the wall of the blood vessel. Thus, the covering part 70 is pressed against the inner wall surface of the blood vessel by the expandable part 22, so that the covering part 70 is fixed inside the blood vessel. Subsequently, the sheath 30 and the pressing shaft 40 are pulled away from the patient's body, with the expanding tool 20 remaining in the body, as illustrated in FIG. 15A.

As soon as the expandable part 22 and the covering part 70 have come into close contact with the inner wall surface of the blood vessel, the blood flow in the blood vessel is blocked or reduced, so that the blood flow is stagnated. In addition, the covering part 70 has overlapping parts 78, so that the sites where the overlapping parts 78 are formed increase in wall thickness and project in the radial direction. Thus, the overlapping parts 78 enhance the effect of controlling the blood flow through the gap between the blood vessel and the covering section 70.

Figure 15B:
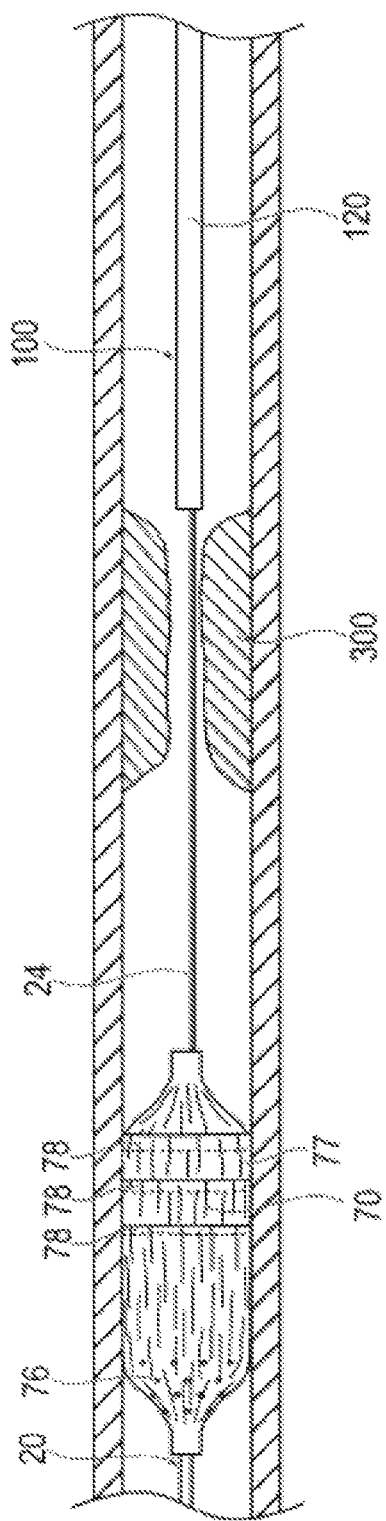

Next, the removing device 100 in which the distal part of the shaft main body 110 including the stirring part 113 has been housed in the outermost sheath body 120 is prepared for use, and the proximal side end part of the shaft part 24 is inserted into the second guide wire lumen 171 of the removing device 100. After that, the removing device 100 is inserted into the proximal side of the thrombus 300, with the help of the shaft part 24 as guide, as illustrated in FIG. 15B. Then, the outermost sheath body 120 is moved toward the proximal side, so that the stirring part 113 expands in the blood vessel, as illustrated in FIG. 16A.

In the next step, a thrombolytic agent is injected into the vicinity of the thrombus 300 in the blood vessel by way of the outermost sheath body 120, the shaft inner tube 112, or the second guide wire lumen 171 (See FIG. 12). The thus injected thrombolytic agent keeps a high concentration and hence produces a thrombolytic effect, because the blood flow is controlled (blocked or reduced) in the region where the thrombus is formed. However, it is not compulsory to use a thrombolytic agent.

After the stirring part 113 has advanced to the vicinity of the thrombus 300, the shaft outer tube 111 is set to rotation by the rotary drive part 130. The stirring part 113 turns together with the shaft outer tube 111. In this way, the thrombus 300 firmly fixed to the blood vessel is crushed.

The stirring part 113 continues to rotate to crush the entire thrombus 300 firmly fixed to the blood vessel because the blood flow is blocked by the medical device 10, as illustrated in FIG. 16B. The segments of a crushed thrombus 301 float without precipitation in the stagnant blood in the blood vessel.

As the stirring part 113 rotates, the rotating force is transmitted to the shaft part 24 inserted into the second guide wire lumen 171. However, since the center axis X of the shaft part 24 is set off from the center axis Y of the inner tube 80 and the expandable part 22 and since the shaft part 24 is constructed such that it hardly rotates, the rotation of the shaft part 24 is restricted and hence this restricts the rotation concerning the center axis Y of the inner tube 80, the expandable part 22, and the covering part 70. This permits the expanding tool 20 to fully produce its effect of controlling the blood flow, which leads to the reduction of burden on the living body.

Figure 17:
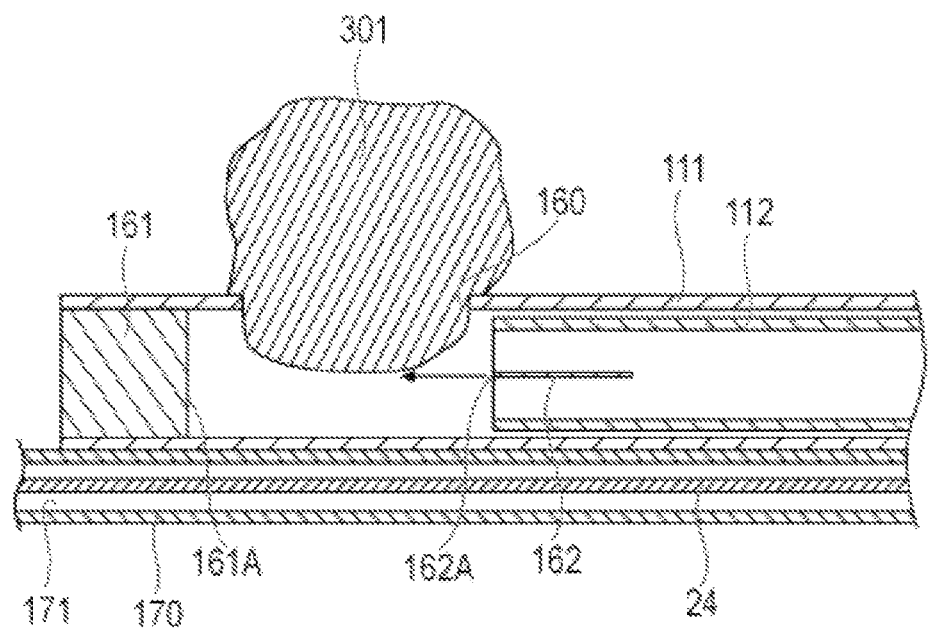
FIG. 17 is an enlarged sectional view illustrating the distal part of the removing device, with the crushed thrombus being sucked into an opening part of an outer tube.

Then, a plunger of the syringe 150 (illustrated in FIG. 11) is pulled out (drawn) so that the hollow part of the shaft inner tube 112 is evacuated to be a negative pressure state. The distal side end part of the shaft inner tube 112 communicates with the hollow part of the shaft outer tube 111. Moreover, the shaft outer tube 111 also communicates with the outside of the shaft main body 110 through the opening part 160. Therefore, the opening part 160 applies a suction force to the outside of the shaft main body 110 and attracts the segments of the crushed thrombus 300 which are floating in the blood vessel. The thrombus portion(s) 301, which has been attracted to the opening part 160, partly enters the hollow part inside of the shaft outer tube 111, as illustrated in FIG. 17.

Figure 18:
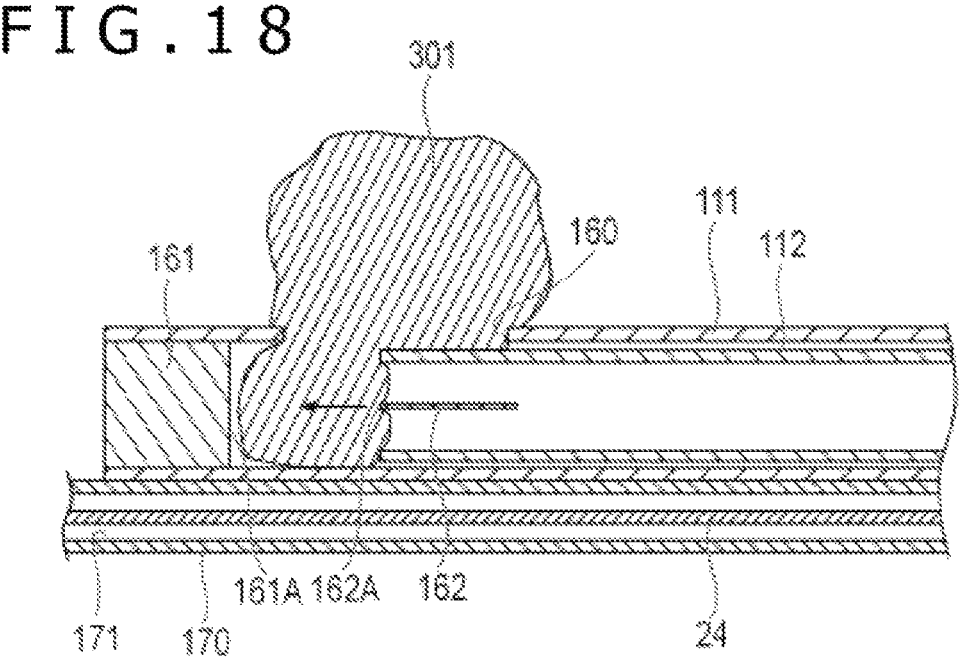
FIG. 18 is an enlarged sectional view illustrating the distal part of the removing device depicting how the inner tube cuts out the thrombus which has been sucked into the opening part of the outer tube.

After the plunger of the syringe 150 is pulled out, the shaft inner tube 112 is moved in the axial direction relative to the shaft outer tube 111. As the shaft inner tube 112 is moved toward the distal side of the shaft outer tube 111 or moved in such a way that the shaft inner tube 112 approaches the attachment part 161 from the proximal side with respect to the opening part 160, a portion of the thrombus portion(s) 301 which has entered the hollow part inside of the shaft outer tube 111 from the opening part 160 is compressed and cut out by the distal face of the shaft inner tube 112, as illustrated in FIG. 18.

Figure 19:
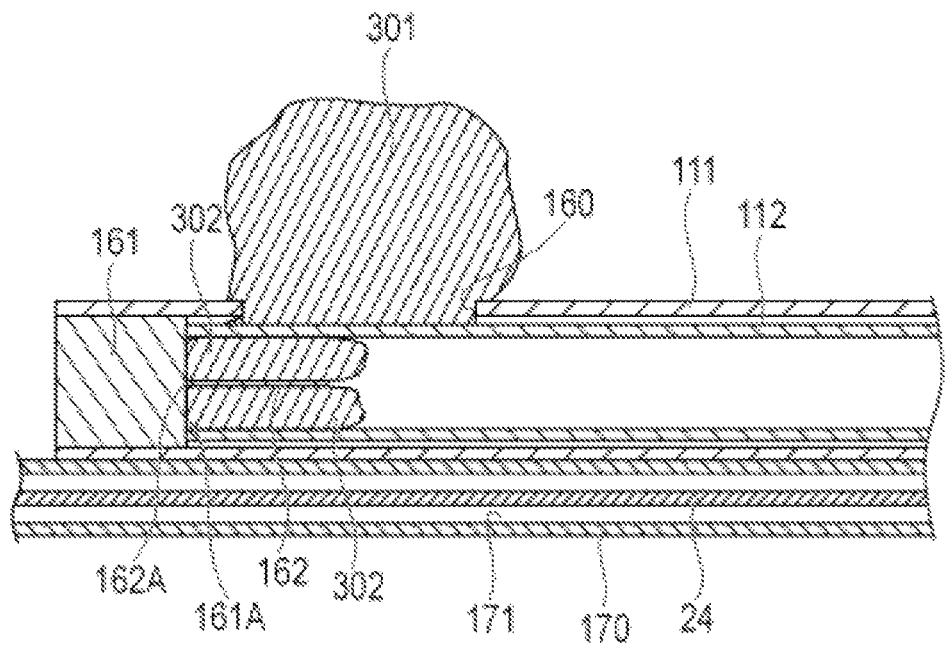
FIG. 19 is an enlarged sectional view illustrating the distal part of the removing device depicting how the thrombus which has been cut out by the inner tube is cut by a cutting part.

The shaft inner tube 112 is moved to such an extent that the distal face of the shaft inner tube 112 comes into contact with the attachment face 161A of the attachment part 161 so that a cut off thrombus portion 302 settles down in the hollow part inside of the shaft inner tube 112, as illustrated in FIG. 19. At this time, the thrombus portion 302 is cut into two parts by the blade 162A of the cutting part 162 which is provided at the distal part of the shaft inner tube 112. As the shaft inner tube 112 comes into contact with the attachment face 161A of the attachment part 161, the blade 162A also comes into contact with the attachment face 161A, and the thrombus portion 302 which has been cut off in the hollow part inside of the shaft outer tube 111 is cut by the blade 162A while it is pressed against the attachment part 161. Therefore, the thrombus portion 302 which has been cut off is surely cut and is made into segments smaller than the inner diameter of the shaft inner tube 112. In this way, it is possible to prevent the cut off thrombus portion 302 from clogging the hollow part inside of the shaft inner tube 112.

Figure 20:
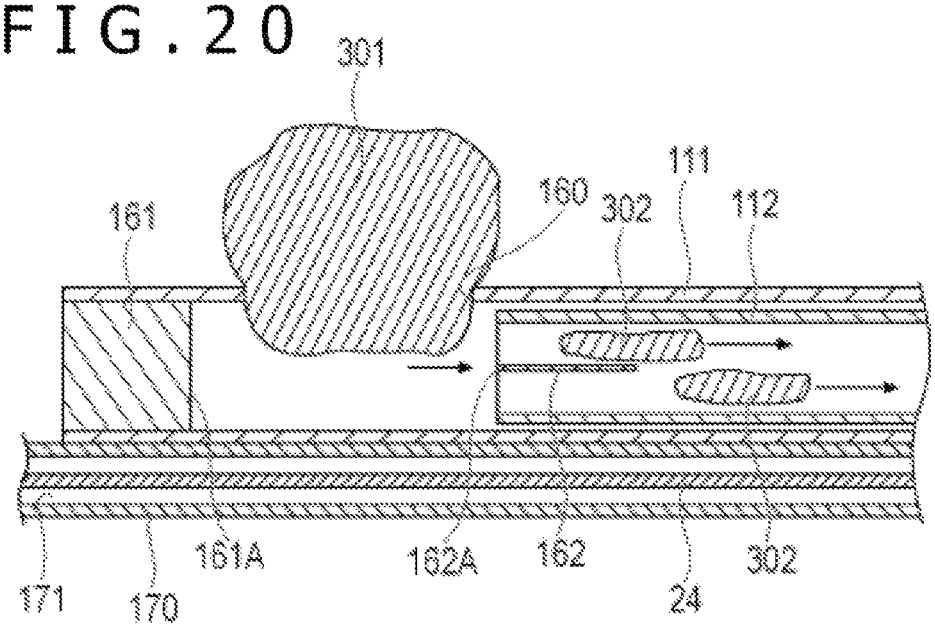
FIG. 20 is an enlarged sectional view illustrating the distal part of the removing device depicting how the thrombus which has been cut by the cutting part is suctioned into a proximal side of the inner tube.

Since the hollow part of the shaft inner tube 112 remains evacuated by the syringe 150 and in the negative pressure state, the sheared thrombus portion 302 moves toward the proximal side of the hollow inside of the shaft inner tube 112, as illustrated in FIG. 20. As the shaft inner tube 112 is moved toward the proximal side from the attachment part 161, the opening part 160 opens again and the thrombus portion(s) 301 is sucked into the hollow part of the shaft outer tube 111. Therefore, the thrombus portion(s) 301 can be cut into small pieces and suctioned continuously by allowing the shaft inner tube 112 to reciprocate in the axial direction repeatedly.

It is desirable that the shaft outer tube 111 keeps rotating while the crushed thrombus portion(s) 301 is being suctioned by the shaft main body 110. The continuously rotating shaft outer tube 111 produces an eddy current in the blood in the blood vessel. Thus, this allows the thrombus portion(s) 301 to gather together near the vicinity of the center around which the thrombus portion(s) 301 turns or the vicinity of the center of the blood vessel in the radial direction. This facilitates the suction of the thrombus portion(s) 301 from the opening part 160. In addition, the eddy current that has occurred in the vicinity of the shaft part outer tube 111 also affects the flow in the hollow part of the shaft inner tube 112, thereby producing the eddy current also inside the shaft inner tube 112. The result is that resistance to flow in the axial direction decreases inside the shaft inner tube 112, thereby allowing the sheared thrombus portion 302 to be suctioned smoothly.

According to the exemplary embodiment, the shaft part outer tube 111 turns and the shaft part inner tube 112 reciprocates in the axial direction along the shaft part outer tube 111 while the thrombus portion(s) 301 is being suctioned in. However, additional movement may also be added.

According to the exemplary embodiment, the blood flow is blocked by the medical device 10, so that the fragments of the crushed thrombus 300 float in the stagnant blood. This leads to the ability to efficiently suction the thrombus portion(s) 301 from the opening part 160 and remove the thrombus portion(s) 301 from the blood vessel without allowing the thrombus portion(s) 301 to flow to another place. In the case where the blood is flowing, a strong suction force is required. However, this is not the case according to the exemplary embodiment, in which the blood flow is blocked and a suction force can be easily applied, so that the thrombus portion(s) 301 can be suctioned and removed more efficiently.

It is also possible to suction the thrombus portion(s) 301 in a different way as illustrated in FIG. 21A. That is, the removing device 100 is pushed against the covering part 70 such that the proximal part of the covering part 70 is depressed, and the thrombus portion(s) 301 sticking to the covering part 70 is suctioned out of the opening part 160.

Figure 22A:
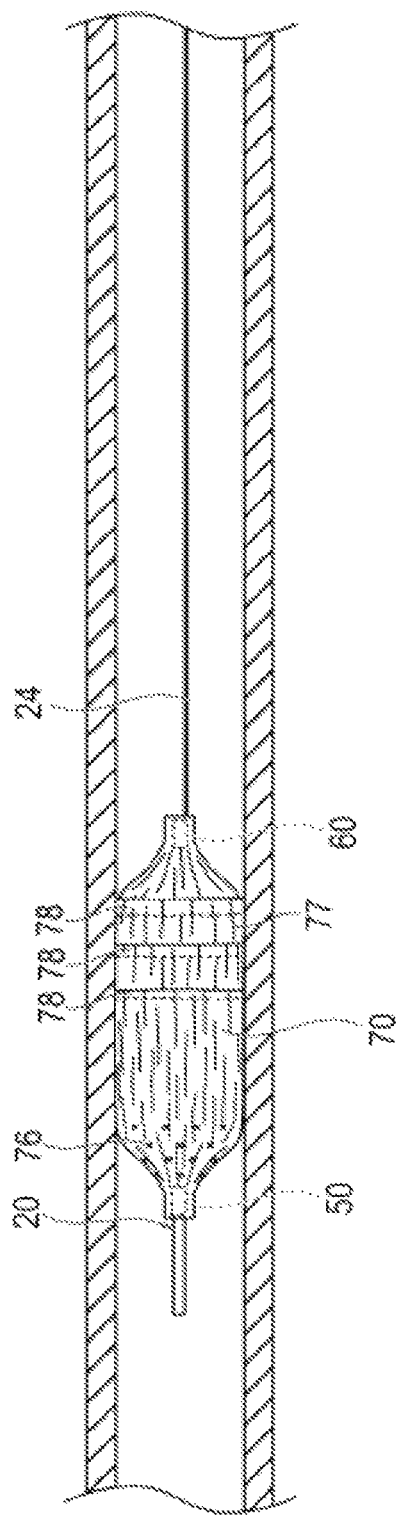

After the suction of the thrombus portion(s) 301 is complete, the reciprocal motion and rotary motion of the shaft part outer tube 111 and the shaft part inner tube 112 are suspended. The outermost sheath body 120 is moved in the axial direction, so that the stirring part 113 is housed, as illustrated in FIG. 21B. After that, the removing device 100 is pulled out from the blood vessel, with the expanding tool 20 remaining, as illustrated in FIG. 22A.

Figure 22B:
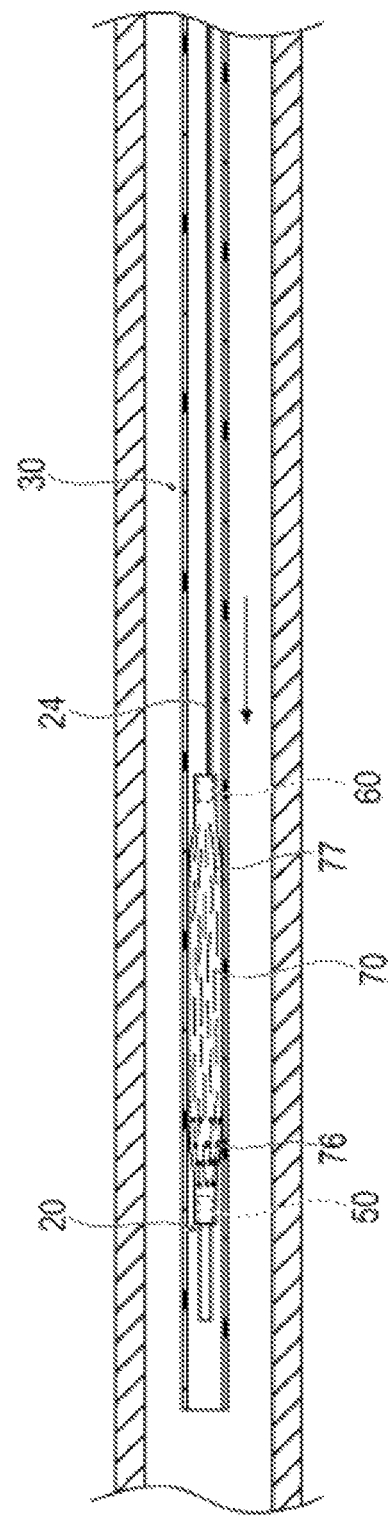

In the next step, the proximal side end part of the shaft part 24 is inserted into the sheath 30 and the sheath 30 is inserted into the blood vessel along the shaft part 24, so that it approaches the vicinity of the expandable part 22 and the covering part 70. Then, as illustrated in FIG. 22B, the sheath 30 is pushed in, with the proximal end part of the shaft part 24 held by hand so as to prevent its movement in the axial direction, and housed into the inside of the sheath 30, with the expandable part 22 and the covering part 70 contracted in diameter. When the covering part 70 is contracted in diameter, the blood inside the covering part 70 is released outward from a hole part 76. When the covering part 70 is housed in the sheath 30, the thrombus portion(s) 301 sticking to the covering part 70 can also be housed in the sheath 30. It is also possible to house the thrombus portion(s) 301, together with the covering part 70, in the sheath 30 after the covering part 70 in contact with the inner wall surface of the blood vessel is moved toward the proximal direction, so that the thrombus portion(s) 301 sticking to the blood vessel is scraped off by the covering part 70.

Figure 23A:
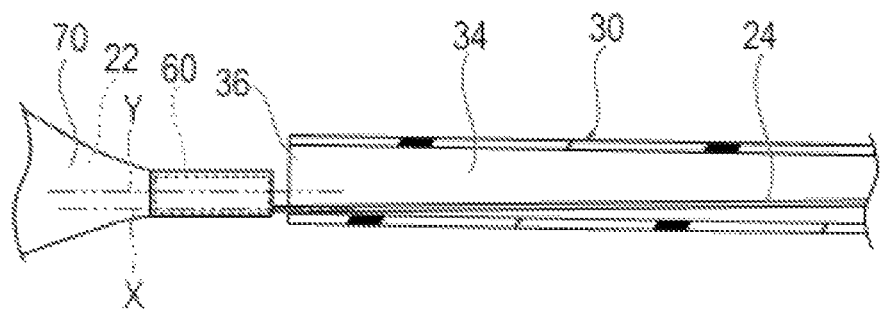

It rarely happens that the sheath 24 is positioned on the center axis of the sheath 30 because the shaft part 24 and the sheath 30 are subject to various external forces. Therefore, the shaft part 24 is likely to be positioned near the inner wall surface at the tubular body opening part 36 of the sheath 30, as illustrated in FIG. 23A. Therefore, the expandable part 22 and the covering part 70 are housed in the sheath 30 in the following way. The shaft part 24 is turned by hand, so that the center axis Y of the expandable part 22 and the inner tube 80 turns relative to the center axis X of the shaft part 24. This operation permits the proximal side connecting part 60 to be positioned close to the center axis side of the sheath 30. Thus, that side with a smaller step between the shaft part 24 and the proximal side connecting part 60 comes into contact with the tubular body opening part 36 of the sheath 30, thereby allowing for smooth housing. In other words, the center axis Y of the expandable part 22 and the inner tube 80 is set off from the center axis X of the shaft part 24, and hence there exists that side with a larger step between the shaft part 24 and the proximal side connecting part 60 and also there exists that side with an extremely small step. Because of this fact, it is possible to smoothly house the expandable part 22 and the covering part 70 in the sheath 30 by rotating the shaft part 24.

Figure 23B:
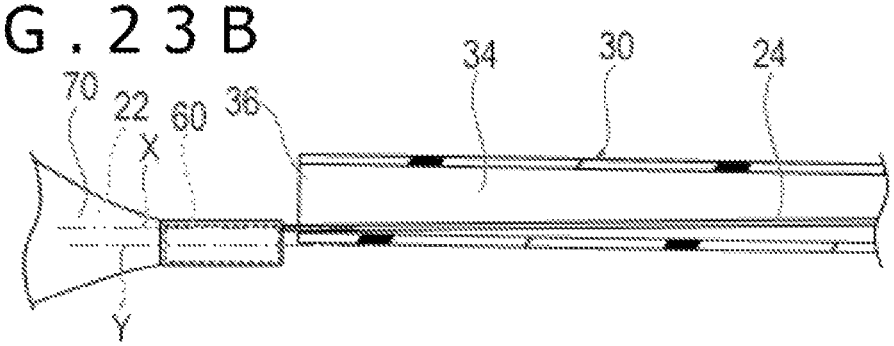

Another arrangement, as illustrated in FIG. 23B, may also be possible, in which the center axis Y of the expandable part 22 and the inner tube 80 rotates around the center axis X of the shaft part 24 as the shaft part 24 is turned by hand, so that the center axis Y is moved to a position which is off set to the outside in the radial direction from the sheath 30. The arrangement like this permits suction by means of the lumen 34 of the sheath 30 or avoids interference by the expandable part 22 and the covering part 70 at the time of releasing a contrast medium into the blood vessel.

Figure 24A:
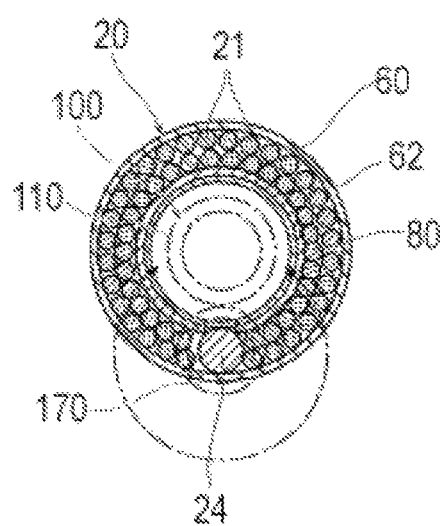
Figure 24B:
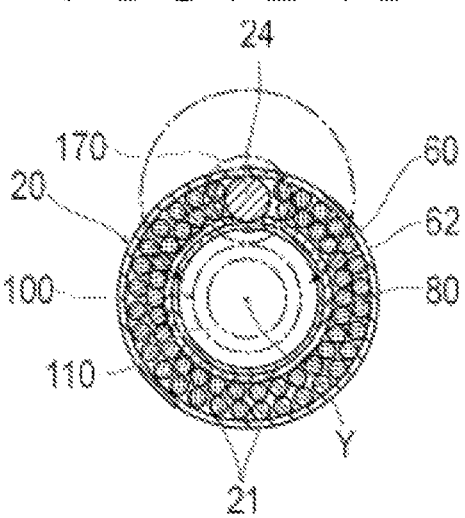

An additional modification may also be possible, in which the removing device 100 is inserted into the blood vessel as a guide for the shaft part 24 of the expanding tool 20 and subsequently the thrombus 300 is crushed and the expanding tool 20 is repositioned for another step of crushing. As illustrated in FIG. 24A, first, the removing device 100 is inserted into the blood vessel as a guide for the shaft part 24, so that the removing device 100 crushes the thrombus 300. Since the shaft part 24 is inserted into the tubular body 170 for guide wire of the removing device 100, the shaft part 110 provided with the stirring part 113 moves around the tubular body 170 for the guide wire as indicated by the one-dot chain line in FIG. 24A. Then, a stirring tool 200 is temporarily housed in the sheath 30, and, for example, after rotation through 180 degrees the stirring tool 200 is pushed out of the sheath 30 again. This step causes the shaft part 24 of the expanding tool 20, which is off set from the center axis Y, to move in the circumferential direction, as illustrated in FIG. 24B. The removing device 100 is inserted into the blood vessel as a guide for the shaft part 24 which has been repositioned and then turned. The result is that the shaft part 110 having the stirring part 113 moves around the tubular body 170 for guide wire into which the repositioned shaft part 24 has been inserted, as indicated by the one-dot chain line in FIG. 24B. Changing the position of the expanding tool 20 in the blood vessel changes the position of the shaft part 24 around which the removing device 100 rotates. This in turn changes the range over which the thrombus 300 is cut by the removing device 100. The operation in this manner makes it possible to cut the thrombus 300 over its broader range.

Subsequently, the expandable part 22 and the covering part 70 are housed in the sheath 30, and then the expanding tool 20 is pulled out together with the sheath 30 of the blood vessel, whereby treatment is completed.

As mentioned above, the medical device 10 according to the exemplary embodiment is a device to be inserted into the lumen of the living body. The medical device 10 has the long shaft part 24 and the cylindrical inner tube 80 (hollow body) which is arranged at the distal part of the shaft part 24 and in which is formed the lumen for insertion of the guide wire 90. The shaft part 24 has its center axis X which is positioned at the position different from the center axis Y of the inner tube 80 in the cross section perpendicular to the center axis X of the shaft part 24. The inner tube 80 forms the slit 82 (housing part) which passes through the inner peripheral surface to the outer peripheral surface and which extends parallel along the center axis Y of the inner tube 80. The shaft part 24 is positioned between the first slit inner surface 82A and the second inner surface 82B, both facing from the outer peripheral surface to the inner peripheral surface in such a way that at least a part of the shaft part 24 composes the slit 82. In the medical device 10 configured as mentioned above, the center axis X of the shaft part 24 and the center axis Y of the inner tube 80 do not coincide with each other. This arrangement makes it more difficult to turn the shaft part 24 than in the case where the center axis X of the shaft part 24 and the center axis Y of the inner tube 80 coincide with each other. The result is that the device suppresses the decrease of its function in the lumen of the living body with reduced burden on the patient. Moreover, due to the fact that the slit 82 of the inner tube 80 is parallel to the center axis Y of the inner tube 80 and a part of the shaft part 24 is positioned in the slit 82, it is possible to make an arrangement in such a way that the center axis X of the shaft part 24 and the center axis Y of the inner tube do not coincide with each other and yet the center axis X and the center axis Y are parallel to each other. In addition, because the center axis X and the center axis Y are parallel to each other, the medical device 10 can be smoothly moved along the guide wire 90 which passes inside the inner tube 80.

In addition, the slit 82 extends parallel to the center axis Y of the inner tube 80, at least at the site of the proximal side of the slit 82. This makes it possible to arrange the distal part of the shaft part 24 at the slit 82 of the proximal side of the inner tube 80 and to position the center axis X of the shaft part 24 and the center axis Y of the inner tube 80 displaced parallel to each other.

In addition, the center axis X of the shaft part 24 is positioned on the outside in the radial direction of the lumen of the inner tube 80. This permits the inner tube 80 to provide as large a lumen as possible, so that the guide wire can be smoothly inserted into the inner tube 80.

In addition, the inner tube 80 is integral with the shaft part 24 which is joined to the first slit inner surface 82A and the second slit inner surface 82B, both constituting the housing part. This allows the shaft part 24 to come into contact with the first slit inner surface 82A and the second slit inner surface 82B for accurate and easy positioning and joining, which in turn leads to a product with high precision and strength. Moreover, the inner tube 80 may be integral with the shaft part 24 which is joined to the angle 87 (see FIGS. 9A and 9B). This allows the shaft part 24, in contact with the angle 87, to be positioned and joined accurately and easily, which in turn leads to a product with high precision and strength.

In addition, the inner tube 80 has the opening part 83, which penetrates from the inner peripheral surface to the outer peripheral surface, at a position different from the position of the slit 82. This allows for access to the inside of the inner tube 80 from the opening part 83, thereby facilitating work for joining the shaft part 24 to the first slit inner surface 82A and the second slit inner surface 82B of the inner tube 80.

In addition, the opening part 83 is positioned at an opposite side to the slit 82, with the center plane V, which passes through the center axis Y of the inner tube 80 and orthogonally crosses the plane on which is positioned both the center axis X and the center axis Y. This allows for easy access to the first slit inner surface 82A and the second slit inner surface 82B through the opening part 83, thereby facilitating work for joining the shaft part 24 to the first slit inner surface 82A and the second slit inner surface 82B from the inside of the inner tube 80.

In addition, the opening part 83 is positioned on the extension of the straight line connecting the center axis Y of the inner tube 80 and the first slit inner surface 82A and the second slit inner surface 82B (or the angle 87). This allows for easy access to the first slit inner surface 82A and the second slit inner surface 82B (or the angle 87) from the opening part 83, thereby facilitating work for joining the shaft part 24 to the first slit inner surface 82A and the second slit inner surface 82B (or the angle 87) from the inside of the inner tube 80.

In addition, the opening part 83 has the first opening part 83A and the second opening part 83B. The first opening part 83A is positioned on the extension of the straight line connecting the first slit inner surface 82A (or the angle 87) to the center axis Y of the inner tube 80. The second opening part 83B is positioned on the extension of the straight line connecting the second slit inner surface 82B (or the angle 87) to the center axis Y of the inner tube 80. This allows for the efficient joining of the first slit inner surface 82A and the second slit inner surface 82B (or the angle 87), which is positioned at the different positions of the slit 82, with the help of the opening parts suitable for each of them.

In addition, the medical device 10 has the cylindrical outer tube 62 (outside hollow body) and the expandable part 22. The cylindrical outer tube 62 is arranged coaxially with the inner tube 80 (hollow body) and outside, in the radial direction, the inner tube 80. The expandable part 22 is variable in shape with the expandable outside diameter and has the proximal end held and fixed between the inner tube 80 and the outer tube 62. Moreover, the center axis Y of the expandable part 22 is positioned at a position different from the position of the center axis X of the shaft part 24 in the cross section perpendicular to the center axis X of the shaft part 24. Therefore, the center axis X of the shaft part 24 and the center axis Y of the expandable part 22 are off set in parallel with each other. As the result, the expandable part 22, which expands to come into contact with the lumen of the living body, hardly rotates and can suppress the decrease of its function in the blood vessel, which leads to reduced burden on the patient.

In addition, the center axis X of the shaft part 24 is positioned between the inner tube 80 and the outer tube 62. Therefore, the center axis X is positioned outside in the radial direction of the lumen of the inner tube 80. This helps expand the lumen of the inner tube 80 as much as possible, thereby allowing the guide wire to be smoothly inserted into the inner tube 80.

In addition, it is desirable that the shaft part 24 does not enter the lumen of the inner tube 80 and the outer peripheral surface of the shaft part 24 coincides with the inner peripheral surface of the inner tube 80 or is positioned outside in the radial direction with respect to the inner peripheral surface of the inner tube 80. This helps expand the lumen of the inner tube 80 as much as possible, thereby allowing the guide wire to be smoothly inserted into the inner tube 80.

Further, the present disclosure is directed to a method for treatment which is performed by inserting the medical device 10 into the lumen of the living body. This method includes a step of inserting the distal part of the medical device 10 into the lumen of the living body, a step of inserting the long sheath 30 (tubular body) along the shaft part 24 into the lumen of the living body, a step of rotating the shaft part 24 relative to the sheath 30 and adjusting the position in the rotating direction of the shaft part, a step of housing the medical device 10 in the sheath 30, and a step of pulling out the medical device 10 from the lumen of the living body. The method for treatment thus configured offers the following advantages. The housing into the sheath 30 can be accomplished after the shaft part 24 has been rotated so as to facilitate the housing into the sheath 30 because the center axis Y of the inner tube 80 (hollow body) is set off from the center axis X of the shaft part 24. Furthermore, the inner tube 80 can be arranged at any position which does not interfere with suction by the sheath 30 or release of contrast medium because the shaft part 24 is capable of rotation.

The disclosure herein is not restricted in its scope to the embodiment just mentioned above; it may be variously modified within its scope by those who are skilled in the art. For example, the exemplary embodiment is designed such that the medical device 10 is accessed in the patient's body through an upstream side of the affected part, but through a downstream side of the affected part may also be possible.

In addition, according to the exemplary embodiment, the device to be inserted into the lumen of the living body along the shaft part 24 is the removing device 100 provided with the stirring part 113. However, the device to be inserted is not restricted to the one mentioned above.

In addition, the medical device 10 may be inserted into not only the lumen of the living body but also the vessel, vasculum, urinary duct, bile duct, oviduct, hepatic duct, and similar passageways.

In addition, as illustrated in FIG. 25A for the modified example, it is not always necessary that the slit 201 of the inner tube 200 (hollow body) extends to the distal side. Alternatively, as illustrated in FIG. 25B for another modified example, the site parallel to the center axis Y of the slit 211, the site being formed in the inner tube 210 (hollow body), may be provided at only the proximal side of the inner tube 210. Despite this configuration, the center axis Y of the inner tube 210 can be parallel to the center axis X of the shaft part 24 if the shaft part 24 is located along the site parallel to the center axis Y of the slit 211.

In addition, as illustrated in FIG. 26 for another modified example, the proximal side connecting part 220 to be provided to the proximal part of the expandable part 22 may be formed such that the proximal side is cut on a slant. In this case, too, an inner tube 221 (hollow body) constituting the proximal side connecting part 220 has its proximal side cut on a slant. The foregoing configuration permits, when the proximal side connecting part 220 is housed in the sheath 30, the proximal side connecting part 220 to be easily housed in the sheath 30 without the possibility that the proximal side connecting part 220 is caught by the sheath 30. This leads to easy housing.

Figure 27:
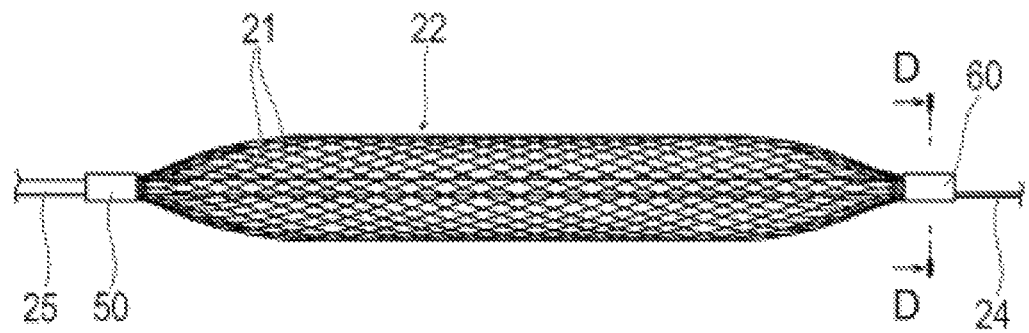
FIG. 27 is a plan view illustrating the expanding tool according to a further example.
Figure 28:
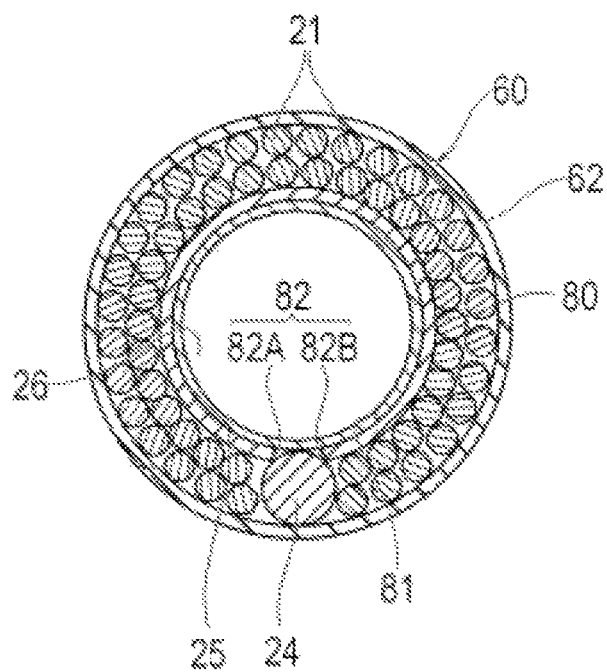
FIG. 28 is a sectional view taken along the line D-D in FIG. 27.

As illustrated in FIGS. 27 and 28 for another modified example, an expanding tool 180 may not be provided with the covering part which covers the expandable part 22. In this case, the reticulate expandable part 22 can function as a filter that controls the passage of the thrombus 301 while allowing for the blood flow.

Figure 29:
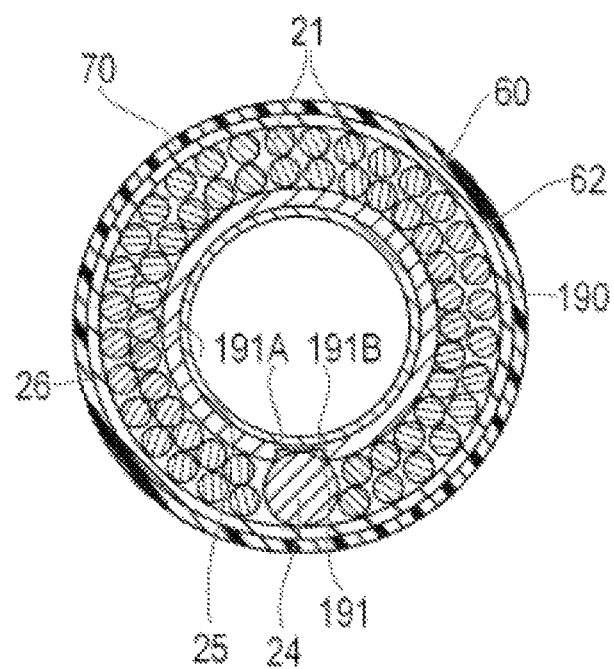
FIG. 29 is a sectional view illustrating the expanding tool as further another example.

In addition, as illustrated in FIG. 29 for another modified example, an inner tube 190 may have a groove 191 (housing part) instead of the slit. The groove 191 is a recess formed on the outer peripheral surface of the inner tube 190 such that it does not penetrate from the outer peripheral surface to the inner peripheral surface. The shaft part 24 is positioned between the two inner surfaces 191A and 191B which face each other and constitute the surface extending from the outer peripheral surface to the inner peripheral surface of the groove 191. The groove 191 may extend from the distal side end part to the proximal side end part, or alternatively, the groove 191 may extend from the position between the distal side end part to the proximal side end part to the proximal side end part. Due to the fact that the site for housing the shaft part 24 is not the slit but the groove 191, the shaft part 24 does not enter the lumen of the inner tube 190. The result is that the lumen of the inner tube 190 has a larger space as to permit the guide wire to be smoothly inserted into the inner tube 190.

In addition, the distal side connecting part 50, the proximal side connecting part 60, and the wires 21 may be made at least partly from a material containing an X-ray contrast medium. For example, a portion of the plurality of wires 21 may be made of a material containing an X-ray contrast medium. The resulting wires help confirm the position of the device during X-ray radiography, which facilitates manipulation. Among preferable X-ray contrast medium is gold, platinum, platinum-iridium alloy, silver, stainless steel, molybdenum, tungsten, tantalum, palladium, and alloys thereof.

In addition, the expanding tool constituting the medical device may not have the tubular body 25 for guide wire and the covering part 70. Moreover, the medical device provided with the shaft part and the hollow body may not have the expandable part capable of expansion in the living body so long as the device is capable of insertion into the lumen of the living body.

The detailed description above describes a medical device and a method for treatment. The invention is not limited, however, to the precise embodiments and variations described. Various changes, modifications and equivalents could be effected therein by one skilled in the art without departing from the spirit or scope of the disclosure as defined by the appended claims. It is expressly intended that all such changes, modifications and equivalents which fall within the scope of the claims are embraced by the claims.

What is claimed is:

1. A medical device configured to be inserted into a lumen of a living body, the medical device comprising:
   a shaft part;
   an expandable part comprising a plurality of wires, the expandable part having a connecting part connected to a distal part of the shaft part;
   the connecting part located at a proximal part of the expandable part and having an inner tube and an outer tube; and
   wherein a distal end portion of the shaft part and a proximal end portion of the plurality of wires are connected between the inner tube and the outer tube.

2. The medical device according to claim 1, wherein the plurality of wires is a plurality of flexible and deformable wires.

3. The medical device according to claim 1, wherein a distal end of the shaft part is located at the proximal part of the expandable part.

4. The medical device according to claim 1, wherein a distal part of the expandable part is movable in an axial direction relative to the connecting part.

5. The medical device according to claim 1, wherein the distal end portion of the shaft part is configured to fix a proximal end portion of the plurality of wires between the inner tube and the outer tube.

6. The medical device according to claim 1, wherein the shaft part is a guide wire.

7. The medical device according to claim 1, wherein the inner tube is a cylindrical hollow body arranged at a distal part of the shaft part and which has a lumen configured for a guide wire to be inserted in the lumen, and wherein the cylindrical hollow body includes a groove depressed from an outer peripheral surface to an inner peripheral surface or a slit penetrating from an outer peripheral surface to an inner peripheral surface.

8. The medical device according to claim 7, wherein the cylindrical hollow body having has a housing part extending along the center axis of the cylindrical hollow body.

9. The medical device according to claim 7, wherein the shaft part is at least partly positioned from the outer peripheral surface to the inner peripheral surface within the slit or the groove of the housing part.

10. The medical device according to claim 8, wherein the housing part extends in a direction parallel to the center axis of the hollow body at least at a proximal side of the housing part.

11. The medical device according to claim 8, wherein the center axis of the shaft part is positioned outside in a radial direction of the lumen of the cylindrical hollow body.

12. The medical device according to claim 7, wherein the shaft part has a center axis at a position which differs from a center axis of the cylindrical hollow body on a cross section perpendicular to the center axis of the shaft part.

13. A method for performing treatment by inserting the medical device defined in claim 1 into the lumen of the living body, the method comprising:
   inserting a long tubular body into the lumen of the living body;
   inserting a distal part of the medical device through the long tubular body into the lumen of the living body and expanding the distal part of the medical device;
   inserting a stirring part along the shaft part of the medical device into the lumen of the living body and expanding the stirring part;
   rotating the stirring part relative to the medical device and the long tubular body;
   pulling out the medical device from the lumen of the living body;
   suctioning with the long tubular body or a removing device; and
   pulling out the medical device from the lumen of the living body.

14. The method for performing treatment according to claim 13, further comprising:
   depressing a proximal portion of the distal part of the medical device.

15. A medical device configured to be inserted into a lumen of a living body, the medical device comprising:
   a shaft part;
   an expandable part comprising a plurality of wires, the expandable part having a proximal side connecting part and a distal side connecting part, the proximal side connecting part being connected to a distal part of the shaft part;
   the proximal side connecting part located at a proximal part of the expandable part and the distal side connecting part located at a distal part of the expandable part; and
   wherein a distal end portion of the shaft part and a proximal end portion of the plurality of wires are fixed between an inner tube and a proximal outer tube, and a distal end portion of the plurality of wires is fixed between the inner tube and a distal outer tube.

16. The medical device according to claim 15, wherein the plurality of wires is a plurality of flexible and deformable wires.

17. The medical device according to claim 15, wherein a distal end of the shaft part is located at the proximal part of the expandable part.

18. The medical device according to claim 15, wherein a distal part of the expandable part is movable in an axial direction relative to the proximal side connecting part.

19. The medical device according to claim 15, wherein the distal end portion of the shaft part is configured to fix a proximal end portion of the plurality of wires between the inner tube and the proximal outer tube.

20. The medical device according to claim 15, wherein the inner tube is a cylindrical hollow body arranged at a distal part of the shaft part and which has a lumen configured for a guide wire to be inserted in the lumen, and wherein the cylindrical hollow body includes a groove depressed from an outer peripheral surface to an inner peripheral surface or a slit penetrating from an outer peripheral surface to an inner peripheral surface.

* * * * *